United States Patent
Mickiewicz et al.

(10) Patent No.: US 8,894,685 B2
(45) Date of Patent: Nov. 25, 2014

(54) FACET FIXATION AND FUSION SCREW AND WASHER ASSEMBLY AND METHOD OF USE

(75) Inventors: Christopher Mickiewicz, Bridgewater, MA (US); Michael Alan Fisher, Middleborough, MA (US); Michael O'Neil, West Barnstable, MA (US); Paul Birkmeyer, Marshfield, MA (US); Sean Selover, Westport, MA (US); Michael Mahoney, Middletown, RI (US); Holly Brideau, West Roxbury, MA (US); Katherine Herard, South Boston, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 434 days.

(21) Appl. No.: 11/734,881

(22) Filed: Apr. 13, 2007

(65) Prior Publication Data

US 2008/0255622 A1    Oct. 16, 2008

(51) Int. Cl.
  *A61B 17/70*    (2006.01)
  *A61B 17/00*    (2006.01)
(52) U.S. Cl.
  CPC ... *A61B 17/7064* (2013.01); *A61B 2017/00004* (2013.01)
  USPC .......................................................... 606/247
(58) Field of Classification Search
  USPC .............. 606/246–249, 280–299, 300–331; 623/17.14
  See application file for complete search history.

(56) References Cited

U.S. PATENT DOCUMENTS

| | | |
|---|---|---|
| 3,934,444 A | 1/1976 | Simons |
| 4,011,602 A | 3/1977 | Rybicki et al. |
| 4,263,904 A | 4/1981 | Judet |
| 4,576,534 A | 3/1986 | Barth et al. |
| 4,590,928 A | 5/1986 | Hunt et al. |
| 4,858,603 A | 8/1989 | Clemow et al. |
| 4,878,794 A | 11/1989 | Potucek |
| 4,898,186 A | 2/1990 | Ikada et al. |
| 4,927,421 A | 5/1990 | Goble et al. |
| 4,961,740 A | 10/1990 | Ray et al. |

(Continued)

FOREIGN PATENT DOCUMENTS

| | | |
|---|---|---|
| EP | 0502698 | 9/1992 |
| EP | 0856293 A1 | 8/1998 |

(Continued)

OTHER PUBLICATIONS

International Search Report and Report Opinion dated Sep. 16, 2008 for PCT/US08/59889.

(Continued)

*Primary Examiner* — Jan Christopher Merene
*Assistant Examiner* — Steven Cotroneo
(74) *Attorney, Agent, or Firm* — Nutter McClennen & Fish LLP

(57) ABSTRACT

A spinal implant including a stabilization member coupled to an elongate member is herein provided. The implant can be configured for placement within a facet joint in an intra-facet or trans-facet configuration. Also, the implant can include a fusion-promoting bioactive material thereby providing a single device capable of spinal stabilization and/or fusion. Furthermore, a method of placing such an implant within a facet joint in an intra-facet or trans-facet orientation is hereby provided.

6 Claims, 24 Drawing Sheets

(56) References Cited

U.S. PATENT DOCUMENTS

| | | | |
|---|---|---|---|
| 4,988,351 A * | 1/1991 | Paulos et al. | 606/232 |
| 5,059,193 A | 10/1991 | Kuslich | |
| 5,100,405 A | 3/1992 | McLaren | |
| 5,129,904 A | 7/1992 | Illi | |
| 5,152,303 A | 10/1992 | Allen | |
| 5,156,616 A | 10/1992 | Meadows et al. | |
| 5,169,400 A | 12/1992 | Muhling et al. | |
| 5,180,388 A | 1/1993 | DiCarlo | |
| 5,275,601 A | 1/1994 | Gogolewski et al. | |
| 5,314,427 A * | 5/1994 | Goble et al. | 606/232 |
| 5,364,400 A | 11/1994 | Rego, Jr. et al. | |
| 5,403,136 A | 4/1995 | Mathys | |
| 5,409,486 A | 4/1995 | Reese | |
| 5,443,509 A | 8/1995 | Boucher et al. | |
| 5,456,685 A | 10/1995 | Huebner | |
| 5,470,334 A | 11/1995 | Ross et al. | |
| 5,487,744 A | 1/1996 | Howland | |
| D368,777 S | 4/1996 | Goble et al. | |
| 5,527,312 A * | 6/1996 | Ray | 606/301 |
| 5,545,163 A | 8/1996 | Miller et al. | |
| 5,558,674 A | 9/1996 | Heggeness et al. | |
| D374,286 S | 10/1996 | Goble et al. | |
| D374,287 S | 10/1996 | Goble et al. | |
| D374,482 S * | 10/1996 | Goble et al. | D24/145 |
| 5,562,672 A | 10/1996 | Huebner et al. | |
| 5,571,104 A | 11/1996 | Li | |
| 5,571,139 A | 11/1996 | Jenkins, Jr. | |
| 5,613,968 A | 3/1997 | Lin | |
| 5,645,547 A | 7/1997 | Coleman | |
| 5,681,311 A | 10/1997 | Foley et al. | |
| 5,697,929 A | 12/1997 | Mellinger | |
| 5,743,912 A | 4/1998 | Lahille et al. | |
| 5,743,914 A | 4/1998 | Skiba | |
| 5,840,078 A | 11/1998 | Yerys | |
| 5,871,486 A | 2/1999 | Huebner et al. | |
| 5,885,300 A | 3/1999 | Tokuhashi et al. | |
| 5,888,228 A | 3/1999 | Knothe et al. | |
| 5,925,047 A * | 7/1999 | Errico et al. | 606/65 |
| 5,947,969 A * | 9/1999 | Errico et al. | 606/308 |
| 5,951,560 A | 9/1999 | Simon et al. | |
| 5,964,761 A | 10/1999 | Kambin | |
| 5,968,047 A | 10/1999 | Reed | |
| 5,989,255 A | 11/1999 | Pepper et al. | |
| 6,007,539 A | 12/1999 | Kirsch et al. | |
| 6,030,162 A | 2/2000 | Huebner | |
| 6,045,554 A | 4/2000 | Grooms et al. | |
| 6,048,343 A | 4/2000 | Mathis et al. | |
| 6,080,157 A | 6/2000 | Cathro et al. | |
| 6,096,060 A | 8/2000 | Fitts et al. | |
| 6,099,529 A | 8/2000 | Gertzman et al. | |
| 6,126,663 A | 10/2000 | Hair | |
| 6,162,225 A | 12/2000 | Gertzman et al. | |
| 6,210,442 B1 | 4/2001 | Wing et al. | |
| 6,214,007 B1 | 4/2001 | Anderson | |
| 6,214,012 B1 | 4/2001 | Karpman et al. | |
| 6,277,149 B1 | 8/2001 | Boyle et al. | |
| 6,280,443 B1 | 8/2001 | Gu et al. | |
| 6,283,973 B1 | 9/2001 | Hubbard et al. | |
| 6,383,187 B2 | 5/2002 | Tormala et al. | |
| 6,402,757 B1 | 6/2002 | Moore, III et al. | |
| 6,461,373 B2 | 10/2002 | Wyman et al. | |
| 6,464,706 B1 * | 10/2002 | Winters | 623/13.14 |
| 6,485,518 B1 | 11/2002 | Cornwall et al. | |
| 6,488,683 B2 * | 12/2002 | Lieberman | 606/263 |
| 6,506,192 B1 | 1/2003 | Gertzman et al. | |
| 6,524,316 B1 * | 2/2003 | Nicholson et al. | 606/326 |
| 6,527,773 B1 | 3/2003 | Lin et al. | |
| 6,540,747 B1 | 4/2003 | Marino | |
| 6,565,572 B2 | 5/2003 | Chappuis | |
| 6,569,186 B1 * | 5/2003 | Winters et al. | 606/232 |
| 6,575,976 B2 | 6/2003 | Grafton | |
| 6,585,518 B1 | 7/2003 | Jenkins et al. | |
| 6,589,245 B1 | 7/2003 | Weiler et al. | |
| 6,629,977 B1 | 10/2003 | Wolf | |
| 6,641,583 B2 | 11/2003 | Shluzas et al. | |
| 6,648,893 B2 | 11/2003 | Dudasik | |
| 6,666,868 B2 | 12/2003 | Fallin | |
| 6,685,706 B2 | 2/2004 | Padget et al. | |
| 6,723,095 B2 | 4/2004 | Hammerslag | |
| 6,730,093 B2 | 5/2004 | Saint Martin | |
| 6,808,526 B1 | 10/2004 | Magerl et al. | |
| 6,811,567 B2 | 11/2004 | Reiley | |
| 6,921,402 B2 | 7/2005 | Contiliano et al. | |
| 6,923,814 B1 | 8/2005 | Hildebrand et al. | |
| 6,945,975 B2 | 9/2005 | Dalton | |
| 6,966,930 B2 | 11/2005 | Arnin et al. | |
| 6,976,818 B2 | 12/2005 | Levey et al. | |
| 6,979,333 B2 | 12/2005 | Hammerslag | |
| 6,981,974 B2 | 1/2006 | Berger | |
| 7,056,341 B2 | 6/2006 | Crozet | |
| 7,090,675 B2 | 8/2006 | Songer | |
| 7,101,398 B2 | 9/2006 | Dooris et al. | |
| 7,108,697 B2 * | 9/2006 | Mingozzi et al. | 606/297 |
| 7,291,149 B1 | 11/2007 | Michelson | |
| 7,410,789 B2 | 8/2008 | Schlosser et al. | |
| 7,491,221 B2 | 2/2009 | David | |
| 7,699,878 B2 | 4/2010 | Pavlov et al. | |
| 7,708,761 B2 | 5/2010 | Petersen | |
| 7,794,484 B2 | 9/2010 | Stone et al. | |
| 7,799,057 B2 | 9/2010 | Hudgins et al. | |
| 7,909,826 B2 | 3/2011 | Serhan et al. | |
| 8,142,503 B2 | 3/2012 | Malone | |
| 2001/0029375 A1 * | 10/2001 | Betz et al. | 606/61 |
| 2002/0042615 A1 * | 4/2002 | Graf et al. | 606/73 |
| 2002/0151895 A1 | 10/2002 | Soboleski et al. | |
| 2002/0177898 A1 | 11/2002 | Crozet | |
| 2002/0183747 A1 | 12/2002 | Jao et al. | |
| 2003/0032960 A1 | 2/2003 | Dudasik | |
| 2003/0040746 A1 | 2/2003 | Mitchell et al. | |
| 2003/0125740 A1 | 7/2003 | Khanna | |
| 2003/0153921 A1 | 8/2003 | Stewart et al. | |
| 2004/0006342 A1 | 1/2004 | Altarac et al. | |
| 2004/0082956 A1 | 4/2004 | Baldwin et al. | |
| 2004/0087948 A1 | 5/2004 | Suddaby | |
| 2004/0111093 A1 | 6/2004 | Chappuis | |
| 2004/0127906 A1 * | 7/2004 | Culbert et al. | 606/72 |
| 2004/0127989 A1 | 7/2004 | Dooris et al. | |
| 2004/0143267 A1 | 7/2004 | Fallin | |
| 2004/0143268 A1 | 7/2004 | Falahee | |
| 2004/0167520 A1 | 8/2004 | Zucherman et al. | |
| 2004/0186475 A1 | 9/2004 | Falahee | |
| 2004/0225292 A1 | 11/2004 | Sasso et al. | |
| 2004/0225360 A1 | 11/2004 | Malone | |
| 2004/0230192 A1 | 11/2004 | Graf | |
| 2004/0249376 A1 | 12/2004 | Hammerslag | |
| 2004/0254575 A1 | 12/2004 | Obenchain et al. | |
| 2004/0260296 A1 | 12/2004 | Kaiser et al. | |
| 2004/0260298 A1 * | 12/2004 | Kaiser et al. | 606/72 |
| 2005/0015060 A1 | 1/2005 | Sweeney | |
| 2005/0027293 A1 * | 2/2005 | LeHuec et al. | 606/61 |
| 2005/0038434 A1 | 2/2005 | Mathews | |
| 2005/0055026 A1 | 3/2005 | Biedermann et al. | |
| 2005/0113929 A1 | 5/2005 | Cragg et al. | |
| 2005/0119657 A1 | 6/2005 | Goldsmith | |
| 2005/0124993 A1 | 6/2005 | Chappuis | |
| 2005/0149030 A1 | 7/2005 | Serhan et al. | |
| 2005/0165399 A1 | 7/2005 | Michelson | |
| 2005/0177240 A1 | 8/2005 | Blain | |
| 2005/0192572 A1 | 9/2005 | Abdelgany et al. | |
| 2005/0192580 A1 | 9/2005 | Dalton | |
| 2005/0197660 A1 | 9/2005 | Haid et al. | |
| 2005/0197700 A1 | 9/2005 | Boehm et al. | |
| 2005/0216016 A1 | 9/2005 | Contiliano et al. | |
| 2005/0222681 A1 | 10/2005 | Richley et al. | |
| 2005/0228384 A1 | 10/2005 | Zucherman et al. | |
| 2005/0234459 A1 | 10/2005 | Falahee et al. | |
| 2005/0234551 A1 | 10/2005 | Fallin et al. | |
| 2005/0234552 A1 | 10/2005 | Reiley | |
| 2005/0240188 A1 * | 10/2005 | Chow et al. | 606/72 |
| 2005/0251256 A1 | 11/2005 | Reiley | |
| 2005/0261770 A1 | 11/2005 | Kuiper et al. | |
| 2005/0267480 A1 | 12/2005 | Suddaby | |
| 2005/0273110 A1 | 12/2005 | Boehm et al. | |
| 2006/0004358 A1 | 1/2006 | Serhan et al. | |

(56) References Cited

U.S. PATENT DOCUMENTS

| | | |
|---|---|---|
| 2006/0004367 A1 | 1/2006 | Alamin et al. |
| 2006/0004448 A1 | 1/2006 | Casey |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0015105 A1 | 1/2006 | Warren et al. |
| 2006/0030948 A1 | 2/2006 | Manrique et al. |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1* | 3/2006 | Pavlov et al. ............ 606/72 |
| 2006/0085068 A1 | 4/2006 | Barry |
| 2006/0089646 A1 | 4/2006 | Bonutti |
| 2006/0095036 A1 | 5/2006 | Hammerslag |
| 2006/0095040 A1 | 5/2006 | Schlienger et al. |
| 2006/0106381 A1 | 5/2006 | Ferree et al. |
| 2006/0111179 A1 | 5/2006 | Inamura |
| 2006/0111779 A1 | 5/2006 | Petersen |
| 2006/0111782 A1 | 5/2006 | Petersen |
| 2006/0122609 A1 | 6/2006 | Mirkovic et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0178743 A1 | 8/2006 | Carter |
| 2006/0190081 A1 | 8/2006 | Kraus et al. |
| 2006/0200137 A1 | 9/2006 | Soboleski et al. |
| 2006/0217713 A1 | 9/2006 | Serhan et al. |
| 2006/0217714 A1* | 9/2006 | Serhan et al. ............ 606/61 |
| 2006/0217715 A1* | 9/2006 | Serhan et al. ............ 606/61 |
| 2006/0235388 A1 | 10/2006 | Justis et al. |
| 2006/0235391 A1 | 10/2006 | Sutterlin |
| 2006/0241597 A1 | 10/2006 | Mitchell et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0264953 A1 | 11/2006 | Falahee |
| 2006/0271054 A1 | 11/2006 | Sucec et al. |
| 2006/0276790 A1 | 12/2006 | Dawson et al. |
| 2006/0276801 A1 | 12/2006 | Yerby et al. |
| 2006/0293658 A1 | 12/2006 | Sharim |
| 2007/0016191 A1 | 1/2007 | Culbert et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0055236 A1 | 3/2007 | Hudgins et al. |
| 2007/0055373 A1 | 3/2007 | Hudgins et al. |
| 2007/0073290 A1 | 3/2007 | Boehm |
| 2007/0118132 A1 | 5/2007 | Culbert et al. |
| 2007/0135814 A1 | 6/2007 | Farris |
| 2007/0233093 A1 | 10/2007 | Falahee |
| 2007/0233113 A1* | 10/2007 | Kaelblein et al. ............ 606/69 |
| 2007/0250166 A1 | 10/2007 | McKay |
| 2008/0086131 A1 | 4/2008 | Daly et al. |
| 2008/0103512 A1 | 5/2008 | Gately |
| 2008/0177334 A1 | 7/2008 | Stinnette |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0275507 A1 | 11/2008 | Triplett et al. |
| 2008/0306537 A1 | 12/2008 | Culbert |
| 2008/0306555 A1 | 12/2008 | Patterson et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012566 A1 | 1/2009 | Fauth |
| 2009/0036926 A1 | 2/2009 | Hestad |
| 2009/0036986 A1 | 2/2009 | Lancial et al. |
| 2009/0099602 A1 | 4/2009 | Aflatoon |
| 2009/0105716 A1 | 4/2009 | Barrus |
| 2009/0112269 A1 | 4/2009 | Lieberman et al. |
| 2009/0125066 A1 | 5/2009 | Kraus et al. |
| 2009/0138053 A1 | 5/2009 | Assell et al. |
| 2009/0192551 A1 | 7/2009 | Cianfrani et al. |
| 2009/0192553 A1 | 7/2009 | Maguire et al. |
| 2009/0270927 A1 | 10/2009 | Perrow et al. |
| 2009/0312763 A1 | 12/2009 | McCormack et al. |
| 2010/0016903 A1 | 1/2010 | Matityahu et al. |
| 2010/0094349 A1 | 4/2010 | Hammer et al. |
| 2012/0010662 A1 | 1/2012 | O'Neil et al. |
| 2012/0010699 A1 | 1/2012 | Vesely |

FOREIGN PATENT DOCUMENTS

| | | |
|---|---|---|
| EP | 1210914 A1 | 6/2002 |
| EP | 1248568 A2 | 10/2002 |
| EP | 1452146 A1 | 9/2004 |
| EP | 1585449 A1 | 10/2005 |
| EP | 1813216 A1 | 8/2007 |
| WO | WO-0041636 A1 | 7/2000 |
| WO | 0062684 A1 | 10/2000 |
| WO | 0141681 A1 | 6/2001 |
| WO | WO 01/41681 | 6/2001 |
| WO | 0234120 A2 | 5/2002 |
| WO | 03007829 A1 | 1/2003 |
| WO | 2004043278 A1 | 5/2004 |
| WO | 2004100808 A1 | 11/2004 |
| WO | 2004110288 A2 | 12/2004 |
| WO | 2005004733 A1 | 1/2005 |
| WO | 2005042036 A2 | 5/2005 |
| WO | 2005060845 A1 | 7/2005 |
| WO | 2005076974 A2 | 8/2005 |
| WO | 2005097005 A1 | 10/2005 |
| WO | 2006007739 A1 | 1/2006 |
| WO | 2006009855 A2 | 1/2006 |
| WO | WO-2006002684 A1 | 1/2006 |
| WO | 2006047707 A2 | 5/2006 |
| WO | 2006057943 A2 | 6/2006 |
| WO | 2006065774 A1 | 6/2006 |
| WO | 2006086241 A2 | 8/2006 |
| WO | 2006096803 A2 | 9/2006 |
| WO | 2006116119 A2 | 11/2006 |
| WO | 2007019710 A1 | 2/2007 |
| WO | 2007041698 A1 | 4/2007 |
| WO | 2007047711 A2 | 4/2007 |
| WO | 2007063399 A1 | 6/2007 |
| WO | 2007075454 A1 | 7/2007 |
| WO | 2007120903 A2 | 10/2007 |
| WO | 2007127610 A1 | 11/2007 |
| WO | 2008124196 A2 | 10/2008 |
| WO | WO-2008153732 A1 | 12/2008 |
| WO | 2009018220 A1 | 2/2009 |
| WO | 2009067486 A2 | 5/2009 |
| WO | WO-2009138053 A1 | 11/2009 |

OTHER PUBLICATIONS

International Search Report and Written Opinion dated Jul. 25, 2008 for PCT/US08/50194.

International Search Report and Written Opinion dated Sep. 24, 2008 for PCT/US08/59866.

Akira Igarashi, M.D., et al., "Inflammatory Cytokines Released from the Facet Joint Tissue in Degenerative Lumbar Spinal Disorders", Spine vol. 29, No. 19, pp. 2091-2095, Lippincott Williams & Wilkins, Inc., Oct. 1, 2004.

Albert C. Schmidt, M.D., et al., "Lumbar Fusion Using Facet Inlay Grafts*", Southern Medical Journal, vol. 68, No. 2., Feb. 1975.

Andrew V. Slucky, M.D., et al., "Less Invasive Posterior Fixation Method Following Transforaminal Lumbar Interbody Fusion: a Biomechanical Analysis", The Spine Journal 6 (2006) 78-85.

Anil Sethi, et al., "Transforaminal Lumbar Interbody Fusion Using Unilateral Pedicle Screws and a Translaminar Screw", Eur Spine J (2009) 18:430-434 DOI 10.1007/s00586-008-0825-4, Mar. 2009.

U.S. Appl. No. 12/834,397 for "Pedicular Facet Fusion Screw With Plate" filed Jul. 12, 2010.

(56) References Cited

OTHER PUBLICATIONS

U.S. Appl. No. 12/834,417 for "Pedicular Facet Fusion Screw With Plate" filed Jul. 12, 2010.
Brain W. Su, MD, et al. "An Anatomic and Radiographic Study of Lumbar Facets Relevant to Percutaneous Transfacet Fixation", Spine vol. 34, No. 11, pp. E384-E390, 2009, Lippincott Williams & Wilkins.
Brian P. Beaubien, BME, et al., "In Vitro, Biomechanical Comparison of an Anterior Lumbar Interdody Fusion with an Anteriorly Placed, Low-Profile Lumbar Plate and Posteriorly Placed Pedicle Screws or Translaminar Screws", Spine vol. 30, No. 16, pp. 1846-1851, © 2005, Lippincott Williams & Wilkins, Inc.
Brian P. Beaubien, BME, et al., "Posterior Augmentation of an Anterior Lumbar Interbody Fusion", Spine vol. 29, No. 19, pp. E406-E412, © 2004, Lippincott Williams & Wilkins, Inc.
Ch. D. Ray, "Transfacet Decompression with Dowel Fixation: a New Technique for Lumbar Lateral Spinal Stenosis", Acta Neurochirurgica, Suppl. 43, 48-54 (1988) © by Springer-Verlag 1988.
D.A. McQueen, M.D. et al., "Knee Arthrodesis with the Wichita Fusion Nail", Clinical Orthopaedics and Related Research, No. 446, pp. 132-139, © 2006 Lippincott Williams & Wilkins.
D.Grob et al., Translaminar screw fixation in the lumbar spine: technique, indications, results, Eur Spine J (1998) vol. 7:178-186, © Springer-Verlag 1998.
David W. Polly, Jr., M.D., et al. "Surgical Treatment for the Painful Motion Segment", Spine vol. 30, No. 16S, pp. S44-S51, © 2005, Lippincott Williams & Wilkins, Inc.
Douglas Burton, M.D., et al., "Biomechanical Analysis of Posterior Fixation Techniques in a 360° Arthrodesis Model", Spine vol. 30, No. 24, pp. 2765-2771, © 2005, Lippincott Williams & Wilkins, Inc.
Frank Kandziora, M.D., et al., "Biomechanical Testing of the Lumbar Facet Interference Screw", Spine vol. 30, No. 2, pp. E34-E39, © 2005, Lippincott Williams & Wilkins, Inc.
Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, Lippincott Williams & Wilkins, Inc., Aug. 2004.
Frank M. Phillips, M.D., et al., "Radiographic Criteria for Placement of Translaminar Facet Screws", The Spine Journal 4 (2004) 465-467.
Hans Trouillier, et al., "A Prospective Morphological Study of Facet Joint Integrity Following Intervertebral Disc Replacement with the CHARITE™ Artificial Disc", Eur Spine J. (2006) vol. 15: 174-182 DOI 10.1007/s00586-005-1010-7, Jul. 2005.
Harri Pihajamäki, et al., "Tissue Response to Polyglycolide, Polydioxanone, Polylevolactide, and Metallic Pins in Cancellous Bone: An Experimental Study on Rabbits", Journal of Orthopaedic Research, Aug. 2006.
Jee-Soo Jang, M.D., et. al., "Clinical Analysis of Percutaneous Facet Screw Fixation after Anterior Lumbar Interbody Fusion", J Neurosurg: Spine 3:40-46, Jul. 2005.
Jee-Soo Jang, M.D., et. al., "Minimally Invasive Transforaminal Lumbar Interbody Fusion with Ipsilateral Pedicle Screw and Contralateral Facet Screw Fixation", J Neurosurg: Spine 3:218-223, Sep. 2005.
John W. Klekamp, et. al., "Cervical Transfacet Versus Lateral Mass Screws: A Biomechanical Comparison", Journal of Spinal Disorders, vol. 13, No. 6, pp. 515-518, 2000, Lippincott Williams & Wilkins, Inc., Philadelphia: Dec. 2000.
Langston T, Holly, M.D., et al., "Percutaneous Placement of Posterior Cervical Screws Using Three-Dimensional Fluoroscopy", Spine vol. 31, No. 5, pp. 536-540, © 2006, Lippincott Williams & Wilkins, Inc.
Lisa A. Ferrara, et al., "A Biomechanical Comparison of Facet Screw Fixation and Pedicle Screw Fixation", Spine vol. 28, No. 12, pp. 1226-1234, Lippincott Williams & Wilkins, Jun. 15, 2003.
Matthijs R. Krijnen, M.D., et al, "Does Bioresorbable Cage Material Influence Segment Stability in Spinal Interbody Fusion?" Clinical Orthopaedics and Related Research, No. 448, pp. 33-38 © 206 Lippincott Williams & Wilkins.
Natalie M. Best, et al., "Efficacy of Translaminar Facet Screw Fixation in Circumferential Interbody Fusions As Compared to Pedicle Screw Fixation", J Spinal Disord Tech, vol. 19, No. 2, Apr. 2006.
Neil Duggal, M.D., et al., "Unilateral Cervical Facet Dislocation: Biomechanics of Fixation", Spine vol. 30, No. 7, pp. E164-E168, © 2005, Lippincott Williams & Wilkins, Inc.
Nicola C. Gries, et al., "Early Histologic Changer in Lower Lumbar Discs and Facet joints and their Correlation", Eur Spine J (2000) 9:23-29 © Springer-Verlag 2000, Feb. 2000.
Philipp Schleicher, M.D., et al., "Biomechanical Evaluation of Different Asymmetrical Posterior Stabilization Methods for Minimally Invasive Transforaminal Lumbar Interbody Fusion", J. Neurosurg: Spine, vol. 9, Oct. 2008.
Sung-Min Kim, M.D., et al., "A Biomechanical Comparison of Supplementary Posterior Translaminar Facet and Transfacetopedicular Screw Fixation after Anterior Lumbar Interbody Fusiion", J Neurosurg (Spine 1) 1:101-107, Jul. 2004.
Th.-M. Markwalder, et al, "Translaminar Screw Fixation in Lumbar Spine Pathology", Acta Neurochir (Wien) (1989) 99: 58-60.
Thomas Tischer, et al., "Detailed Pathological Changes of Human Lumbar Facet joints L1-L5 in Elderly Individuals", Eur Spine J Mar. 2006;15(3):308-15, Epub July, vol. 15, 2005.
Yasuaki Tokuhashi, M.D., et al., "C1-C2 Intra-articular Screw Fixation for Atlantoaxial Posterior Stabilization", Spine vol. 25, No. 3, pp. 337-241, Lippincott Williams & Wilkins, Inc., Feb. 1, 2000.
Youn-Kwan Park, M.D., "Facet Fusion in the Lumbosacral Spine: A 2-year Follow-Up Study", vol. 51, No. 1, Jul. 2002.
Youssef masharawi, PhD, BPT, et al., "Facet Tropism and Interfacet Shape in the Thoracolumbar Vertebrae", Spine vol. 30, No. 11, pp. E281-E292, © 2005, Lippincott Williams & Wilkins, Inc., Aug. 15, 2004.
Youssef Masharawi, PhD, et al., "Facet Orientation in the Thoracolumbar Spine", Spine vol. 29, No. 16, pp. 1755-1763, © 2004, Lippincott Williams & Wilkins, Inc.
Yukihiro Kai, M.D., et al., "Posterior Lumbar Interbody Fusion Using Local Facet Joint Autograft and Pedicle Screw Fixation", Spine vol. 29, No. 1, pp. 41-46, Lippincott Williams & Wilkins, Inc., Jan. 1, 2004.
Extended European Search Report issued Nov. 7, 2011 for Application No. 08745489.8 (4 pages).
International Search Report and Written Opinion mailed Nov. 9, 2011 for Application No. PCT/US2011/042335 (16 pages).
International Preliminary Report on Patentability mailed Jan. 24, 2013 for Application No. PCT/US2011/042335 (13 Pages).
European Office Action for Application No. 08745489.8, issued Mar. 27, 2014 (6 pages).

* cited by examiner

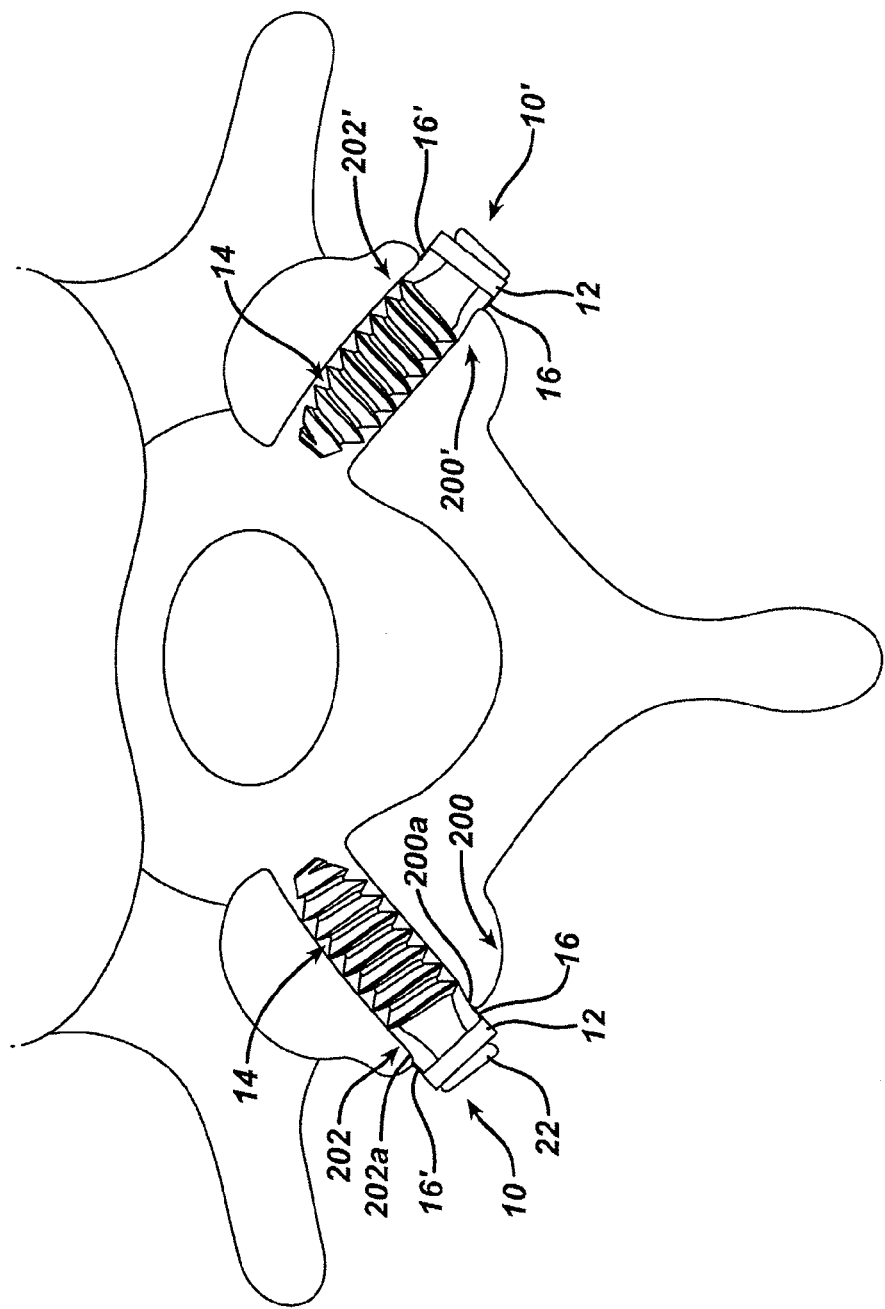

FACET FIXATION AND FUSION SCREW AND WASHER ASSEMBLY AND METHOD OF USE

FIELD OF THE INVENTION

The present invention relates to methods and devices for spinal stabilization and fusion, and particularly to stabilization and fusion of a facet joint.

BACKGROUND OF THE INVENTION

The vertebrae in a patient's spinal column are linked to one another by the intevertebral disc and the facet joints. This three joint complex controls the movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebrae form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. In the lumbar spine, for example, one form of treatment to stabilize the spine and to relieve pain involves fusion of the facet joint.

One known technique for stabilizing and treating the facet joint involves a trans-facet fusion in which pins, screws or bolts penetrate the lamina to fuse the joint. Such a technique has associated with it the risk of further injury to the patient as such translamina facet instrumentation can be difficult to place in such a way that it does not violate the spinal canal and/or contact the dura of the spinal cord or the nerve root ganglia. Further, trans-facet instrumentation has been known to create a rotational distortion, lateral offset, hyper-lordosis, and/or intervertebral foraminal stenosis at the level of instrumentation.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances these implants can result in some degree of foraminal stenosis.

Accordingly, there is a need for instrumentation and techniques that facilitate the safe and effective stabilization of facet joints.

SUMMARY OF THE INVENTION

Spinal implants and methods relating to stabilization and/or fusion of a facet joint via trans-facet and intra-facet delivery of the implants are provided. In general, the implant functions as a sort of mechanical staple and/or key that prevents sliding motion between the diarthroidal surfaces of the facet joint. Further, the spinal implant can include a fusion-promoting bioactive material thereby providing for a single spinal implant capable of allowing for both fixation and fusion of a desired facet joint. Various aspects of the implants and methods are summarized immediately below.

In one aspect, the spinal implant includes an elongate member (e.g., an elongate screw) extending from a distal tip to a proximal end having a head formed thereon. The elongate member can further include a threaded portion. The spinal implant also includes a stabilization member coupled to the elongate member. The stabilization member includes a bone contacting surface being configured to seat the elongate member. In one aspect, the stabilization member is capable of polyaxial motion relative to a longitudinal axis of the elongate member thereby allowing for a better fit of the implant within the facet joint. Additionally, the stabilization member includes at least one feature configured to stabilize at least one of an anatomical structure (e.g., the facet joint) and the spinal implant.

Various embodiments of such stabilization members and features are provided herein. For example, the stabilization member can include at least one tine extending from the stabilization member. The tine can be configured to engage (e.g., pierce) an outer portion of a facet joint as the spinal implant is positioned within the facet joint. Also, the feature can be an elongate feature adapted to be positioned between the facet faces and adjacent the elongate member. In other embodiments, the stabilization member can include at least one feature capable of being positioned within the facet joint and at least one feature (e.g., tine) capable of engaging an outer portion of the facet joint.

In another aspect, the stabilization member can include at least one lateral extension adapted to secure the implant to the facet joint. For example, the lateral extension can include an opening adapted to receive a fixation member (e.g., a screw, pin, etc.), or the extension can include at least one or a plurality of protrusions capable of piercing an underlying vertebra. In another embodiment, the stabilization member can further include a second lateral extension on the stabilization member. In such an embodiment, the first extension can be positioned in communication with a first outer portion of the facet joint (e.g., a first vertebra) while the second lateral extension can be positioned in communication with a second outer portion of the facet joint (e.g., a second vertebra).

In another aspect, at least one component of the implant (e.g., the elongate member, stabilization member, and/or stabilizing feature) can include (e.g., be formed of, include a coating, and/or be housed within a cage-like configuration) a fusion-promoting bioactive material. The fusion-promoting bioactive material can be any material capable of actively participating in spinal fusion. As such, the implant can provide a single device capable of providing both spinal fixation and fusion.

In another aspect, the spinal implant can include an elongate member coupled to a stabilization member so as to allow for polyaxial motion of the member relative to the elongate member. The stabilization member can encircle a portion of the elongate member such that a longitudinal axis of the elongate member passes through an opening of the stabilization member. Further, the stabilization member can be adapted to securely engage a bony portion (e.g., an inner face, an outer edge, etc.) of a facet joint so as to secure the implant relative to the facet joint.

In another aspect, a method for spinal stabilization and/or fusion is provided. The method includes surgically delivering (e.g., in a minimally invasive manner) a spinal implant to a facet joint (in an intra-facet or trans-facet configuration). The implant includes an elongate member having a threaded portion adapted for intra-facet delivery. The elongate member is coupled to a stabilization member having a bone contacting surface being configured to seat the elongate member. The stabilization member includes at least one (or any number of) feature(s) configured to stabilize a portion of the facet joint and the spinal implant. As mentioned above, the feature can include various shapes and/or sizes. Optionally, the method can include delivering a first spinal implant to a first facet joint, and a second implant to a second, corresponding facet joint at the same level of a spine.

These aspects and others will be described in detail below.

BRIEF DESCRIPTION OF THE DRAWINGS

The invention will be more fully understood from the following detailed description taken in conjunction with the accompanying drawings, in which:

FIG. 16A is a representation of the implant of FIG. 15 being positioned within the facet joint in an intra-facet configuration;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, spinal implants and methods for spinal stabilization and/or fusion are provided. The implants are configured for intra-facet and/or trans-facet delivery to the facet joint. Regarding intra-facet delivery, the implant is configured to be placed in the plane of the facet joint, between the diarthroidal surfaces of the facet joint and as a mechanical spacer to distract the facet faces and relieve foraminal stenosis. As such, the implants function as a sort of mechanical key that prevents sliding motion between the diarthroidal joint surfaces. The implants also stabilize the joint by distracting the facet faces and placing the joint capsule in tension. Such distraction of the facet face is believed to contribute to alleviating intervertebral foraminal stenosis. Also, the implants can be adapted so as to constrain rotational motion at the level of the implant placement when placed bilaterally.

Figure 1A:
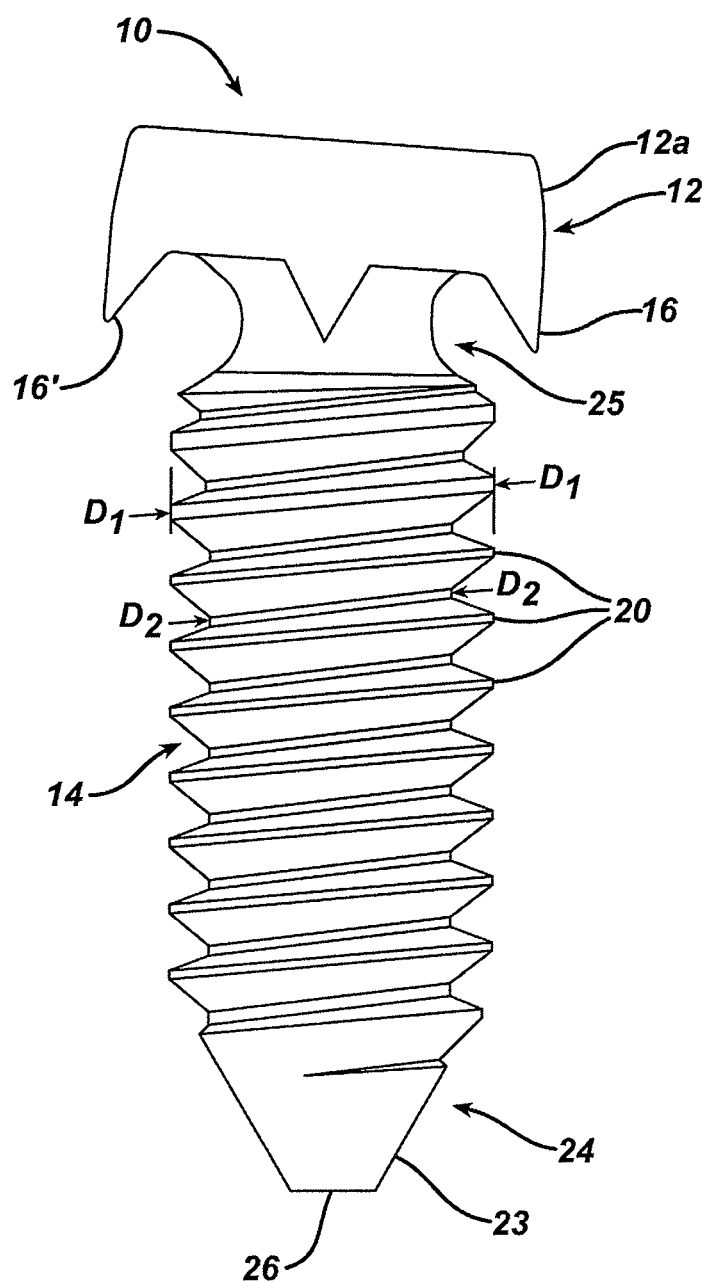
FIG. 1A is a front view of an exemplary embodiment of a spinal implant according to one aspect of the invention.
Figure 1B:
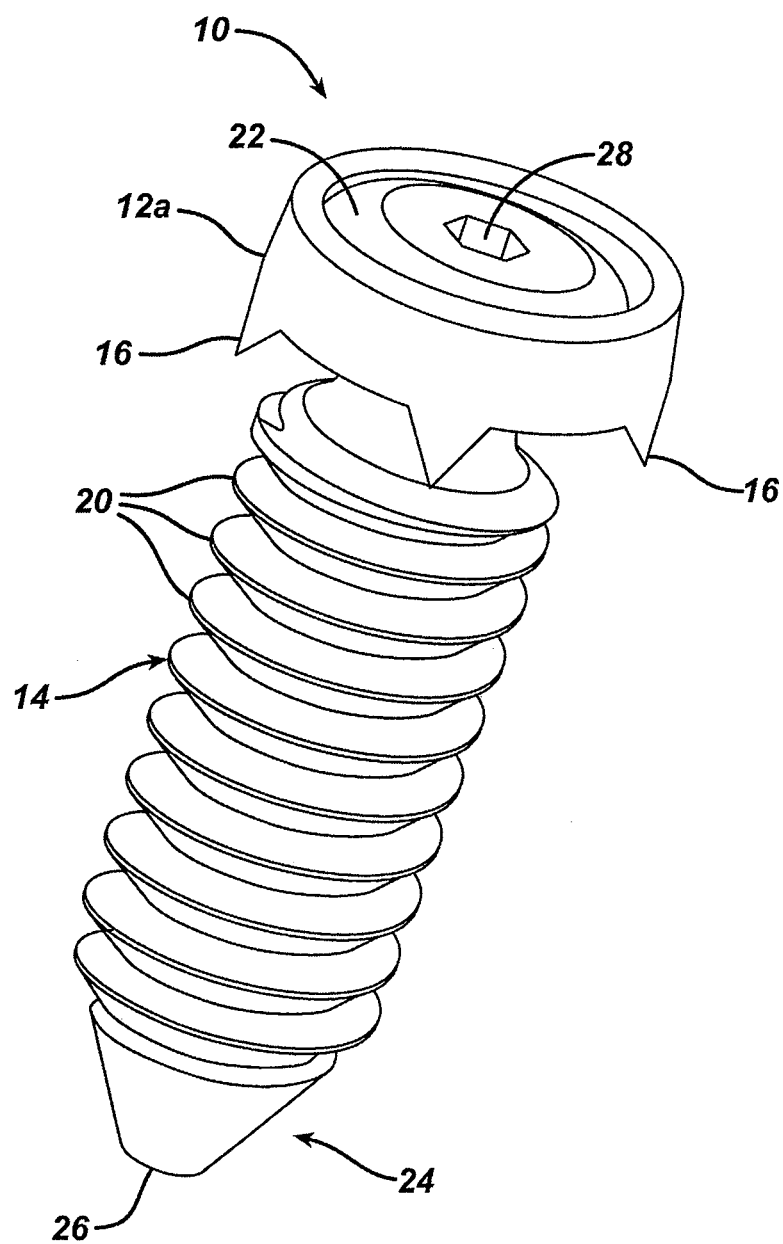
FIG. 1B is a perspective view of the spinal implant of FIG. 1A.
Figure 1C:
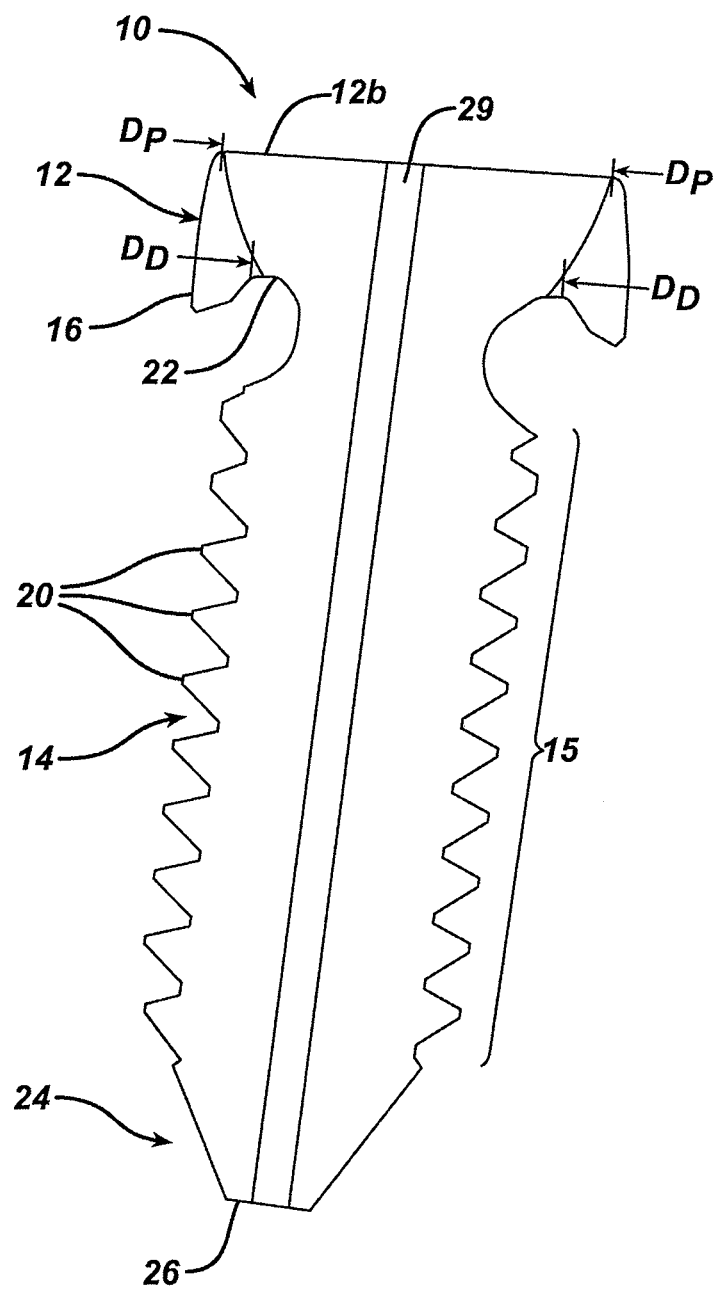
FIG. 1C is a cross-sectional view of the spinal implant of FIG. 1A.
Figure 1D:
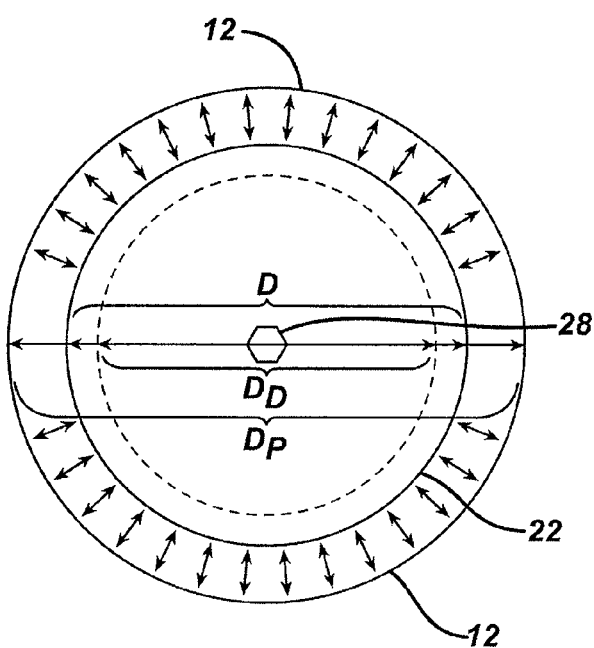
FIG. 1D is a top view of the spinal implant of FIG. 1A.

FIGS. 1A-1D provide an overview of a spinal implant having an elongate member 14 coupled to a stabilization member 12. In an exemplary embodiment, the elongate member 14 is an elongate screw. As shown, the screw 14 extends from a distal 24 to a proximal end 25 which extends to form a screw head 22. At the screw head 22, the implant is coupled to a stabilization member 12. The stabilization member 12 includes a bone contacting surface 12a being configured to seat the screw 14 such that the head 22 of the screw 14 can contact a surface 12b (see FIG. 1C) of the stabilization member 12 opposite the bone contacting surface 12a. In an exemplary embodiment, the stabilization member 12 is polyaxially coupled to the screw head 22 thereby allowing the stabilization member 12 to adapt to various anatomical structures (e.g., facet joint) during intra-facet placement within the facet joint. For example, the stabilization member 12 can be washer-shaped so as to encircle a proximal portion of the screw 14. As shown in FIGS. 1C-1D, the stabilization member 12 can include a proximal opening having a first diameter ($D_P$) and a distal opening having a second diameter ($D_D$) (indicated by dashed lines in FIG. 1D) wherein the openings allow for passage of the screw 14 there-between. The diameter of the distal opening ($D_D$) can be less than a diameter of the screw head 22 (D) thereby retaining the stabilization member 12 to the substantially spherical bottom portion of the screw head 22. Furthermore, the diameter ($D_P$) of the proximal opening of the stabilization member 12 can be greater than the diameter of the screw head 22. As such, the spherical bottom portion of the screw head 22 seated in such a stabilization member 12 enables the desired polyaxial motion of the stabilization member 12 relative to the screw head 22 (as indicated by the plurality of double-headed arrows in FIG. 1D). Providing such a polyaxial coupling provides greater versatility of the spinal implant 10 because the stabilization member 12 can adjust to anatomical structures of various shapes thereby allowing for a better fit of the implant 10. Other embodiments, as will be discussed below, do not provide such a polyaxial coupling but rather provide a substantially rigid coupling of the member 12 to the elongate member. Those skilled in the art will appreciate that any such manner of coupling the stabilization member to the elongate screw is within the spirit and scope of the present invention.

As mentioned above, the stabilization member 12 can include at least one feature 16 capable of stabilizing the implant 10 to an anatomical structure (e.g., a facet joint, tissue, etc.). The stabilization member 12 can include any number of such features 16 (e.g., 1, 2, 3, 4, 5, 6, 7, etc.). Additionally, the stabilization member 12 can include any orientation of such features 16 relative to the member 12. For example, the features 16 can be equally spaced around a circumference of the stabilization member 12 thereby allowing for the implant 10 to engage opposing faces of the facet joint, and adding to the overall stability of the implant 10. In other embodiments, a number of (or one) features 16 can be provided on only one side of the stabilization member 12. Also, the features 16 can include various sizes, configurations, dimensions, etc. Further, a single stabilization member 12 can include features of different configurations, sizes, etc. The following describes various examples of such stabilization members and/or features. Various aspects of each of the following examples can be incorporated into a single implant. Additionally, various alternatives to the implants provided below are clearly within the spirit and scope of the present invention.

Referring to FIGS. 1A-1C, the stabilization member 12 includes a plurality of features configured as tines 16, 16' adapted to pierce an outer portion of the facet joint. As shown, each tine 16, 16' can extend (e.g., substantially downward) from the stabilization member 12. In this embodiment, the tines 16, 16' can be adapted to engage (e.g., contact and/or pierce) an outer portion (e.g., an edge) of a facet joint as the implant 10 is positioned within the facet joint in an intra-facet configuration. As shown in FIG. 1A, a first tine 16 can be positioned on a first side of the member 12, while a second tine 16' can be positioned on an opposite side on the member 12. When so positioned, the first tine 16 can pierce a top vertebra (or top facet face) while the second tine 16' can pierce an adjacent, bottom vertebra (or opposing facet face). As such, the stabilization member 12 can effectively act in a staple-like manner securing the implant 10 within the facet joint.

Figure 2:
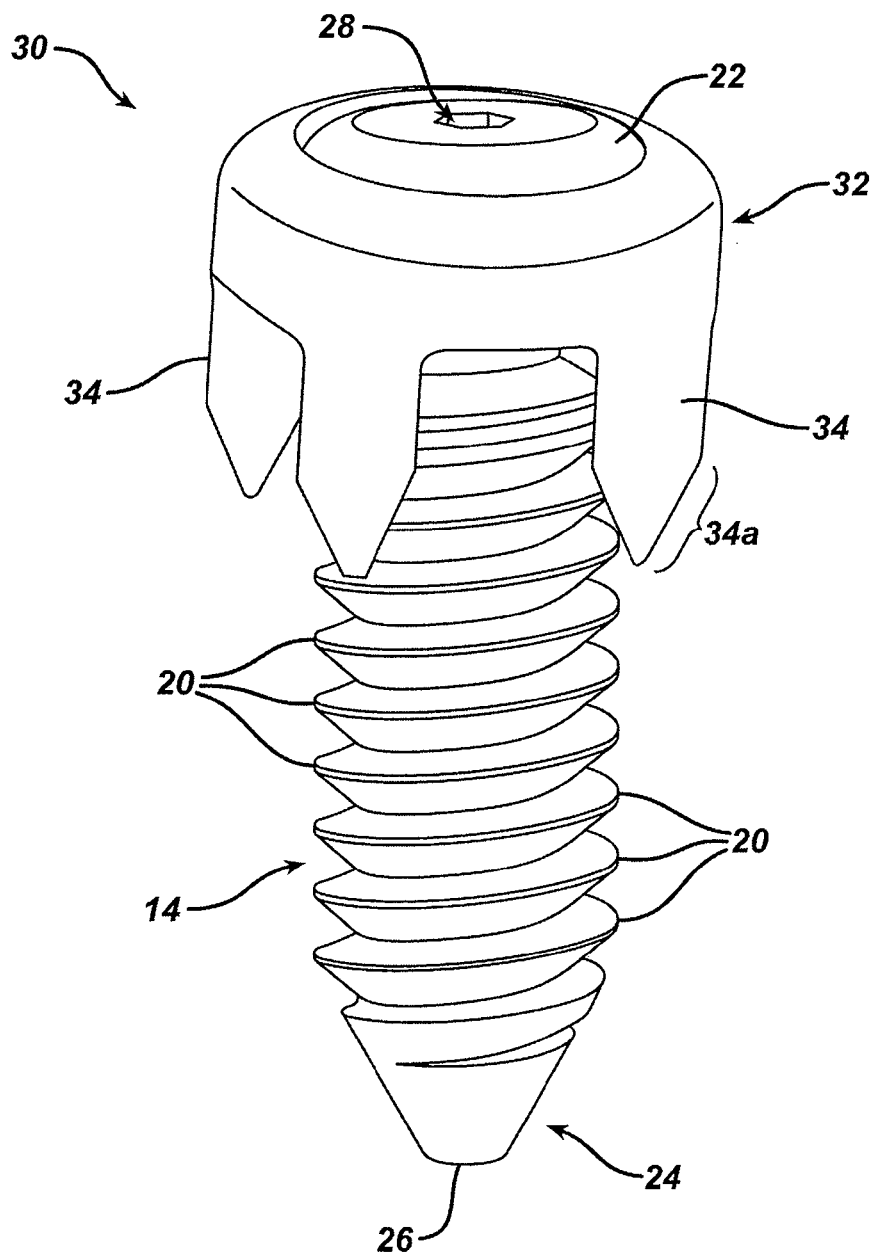
FIG. 2 is a perspective view of an alternative embodiment of a spinal implant.
Figure 3:
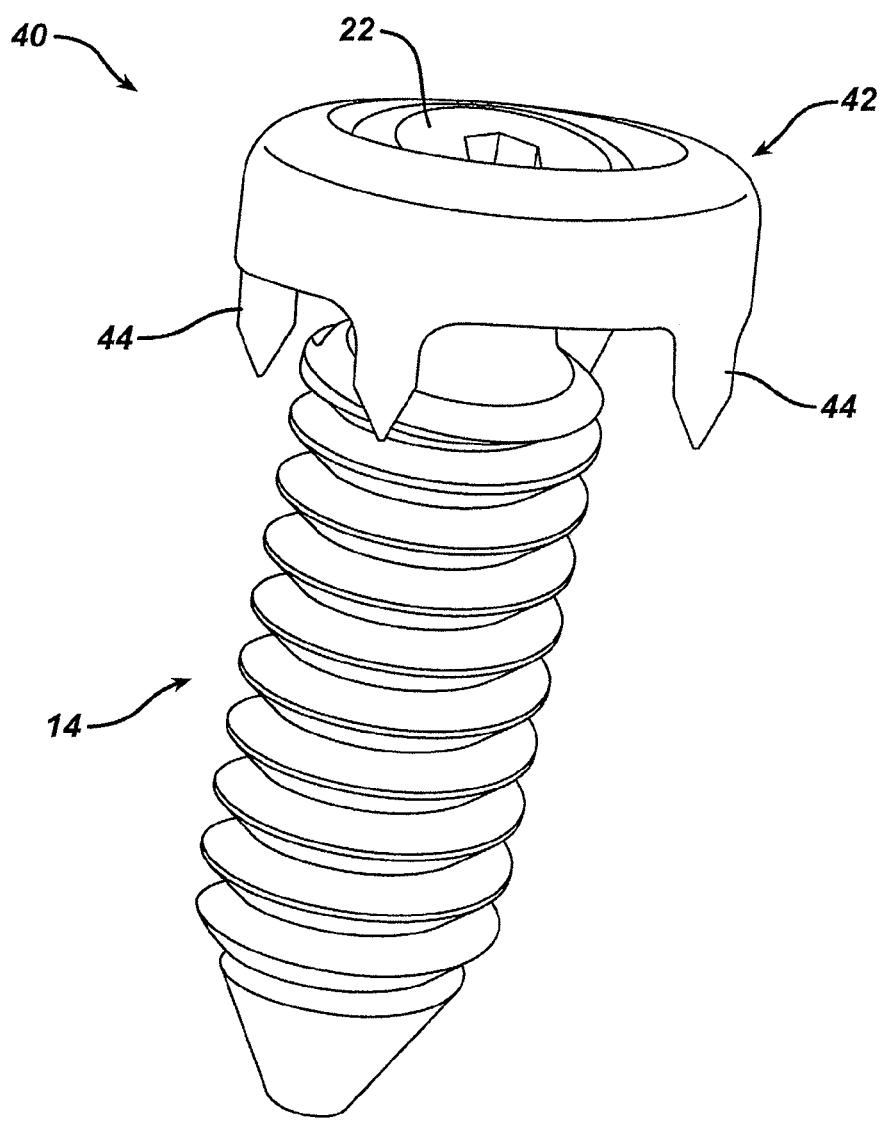
FIG. 3 is a perspective view of another embodiment of a spinal implant.

FIG. 2 provides an alternative spinal implant 30 wherein the stabilization member 32 includes a plurality of features configured as column-shaped tines 34. As shown, each tine 34 includes a tapered distal end 34a thereby facilitating engagement of the tine 34 to a portion of the facet joint. For example, the tine 34 can be adapted to wedge in between the screw 14 and an outer edge of the facet joint thereby securing the implant 30 to the joint. Like the embodiment of FIGS. 1A-1D, the stabilization member 32 can be adapted to include any number of tines 34 placed at any position along the circumference of the stabilization member 32. FIG. 3 provides another spinal implant 40 having a stabilization member 42 with a plurality of tines 44. As shown, the tines 44 are similar to the tines 34 of FIG. 2. However, the tines 44 of FIG. 3 are configured with smaller dimensions (e.g., width and length) as compared to the embodiment of FIG. 2. As such, the tines can be adapted to include any size and/or shape as required so as to be compatible with a target facet joint.

Figure 4:
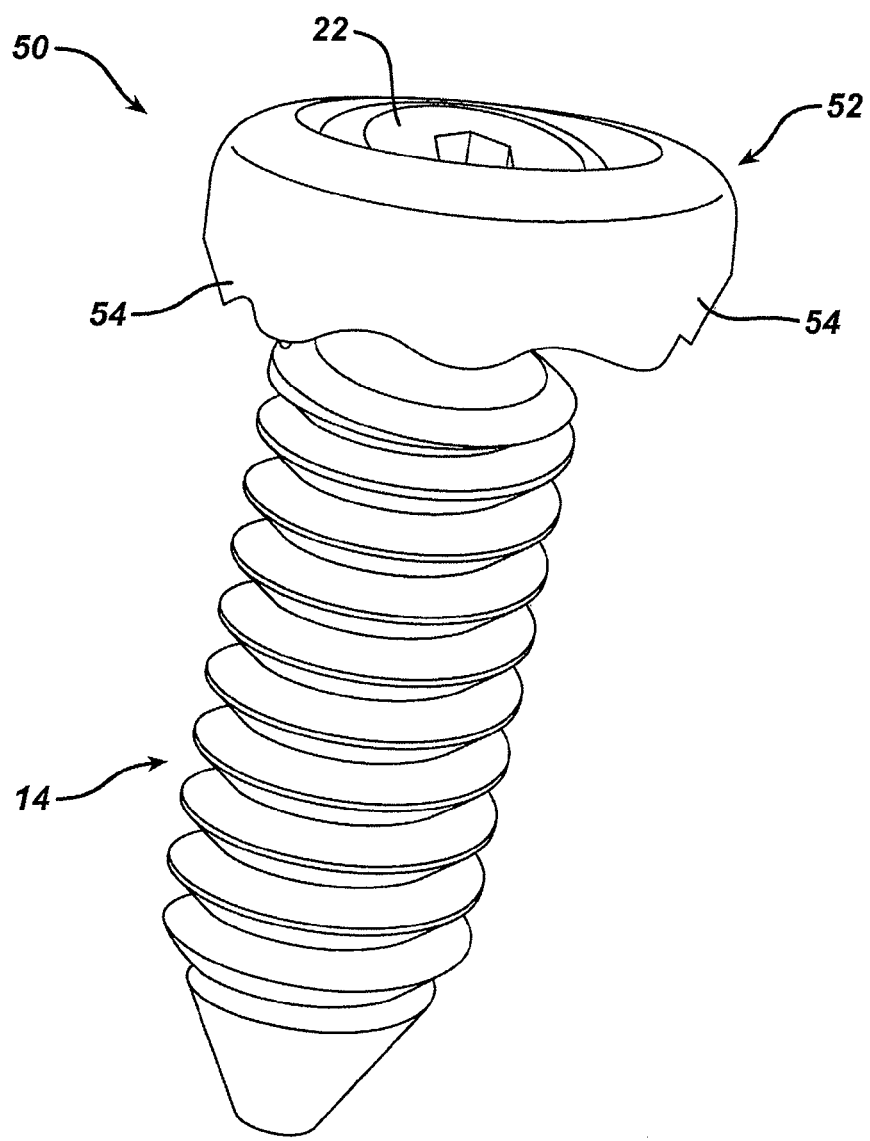
FIG. 4 is a perspective view of another embodiment of a spinal implant.

FIG. 4 provides another spinal implant 50 wherein the stabilization member 52 includes a plurality of tines 54 adapted to provide a substantially serrated edge. The serrated edge can engage and/or cut into an outer portion (or wall) of the facet joint as the implant 50 is positioned in an intra-facet orientation. Although the tines 54 are shown to have a blunt distal-facing end, it is understood that this end of the tine 54 can be alternatively or additionally sharp.

Figure 5:
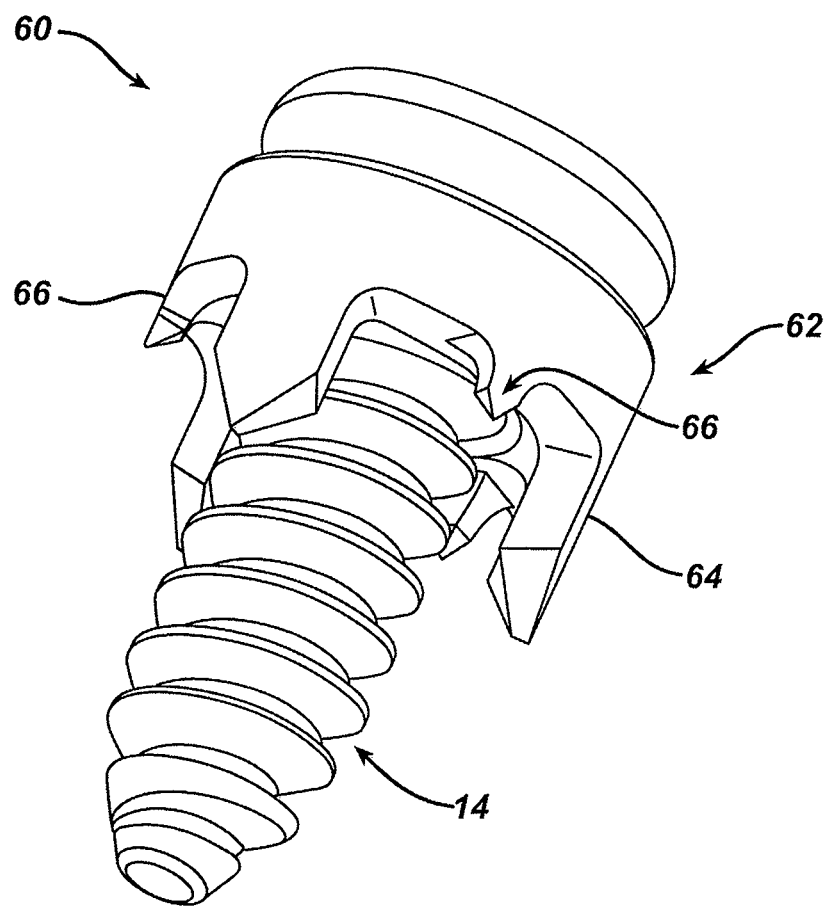
FIG. 5 is a perspective view of another embodiment of a spinal implant.

As mentioned, embodiments of the spinal implant can also include more than one type (or configuration) of feature incorporated into the same stabilization member. For example, FIG. 5 provides a spinal implant 60 having a stabilization member 62 which incorporates tines of various sizes and/or configurations. More specifically, the stabilization member 62 includes at least one tine 64 and at least one tine 66 wherein the tines 64, 66 are different. For example, the tines 64, 66 can be of different sizes, shapes, adapted to perform different functions, etc. In this embodiment, the first tine 64 and second tine 66 are similar in shape but distinct in size. As such, the larger tines 64 can be adapted to wedge between the screw 14 and a bony portion (e.g., an outer edge) of the facet joint while the smaller tines 66 can pierce the outer edge of the facet joint. The tines 64, 66 can also be adapted to vary in both size and configuration.

Figure 6:
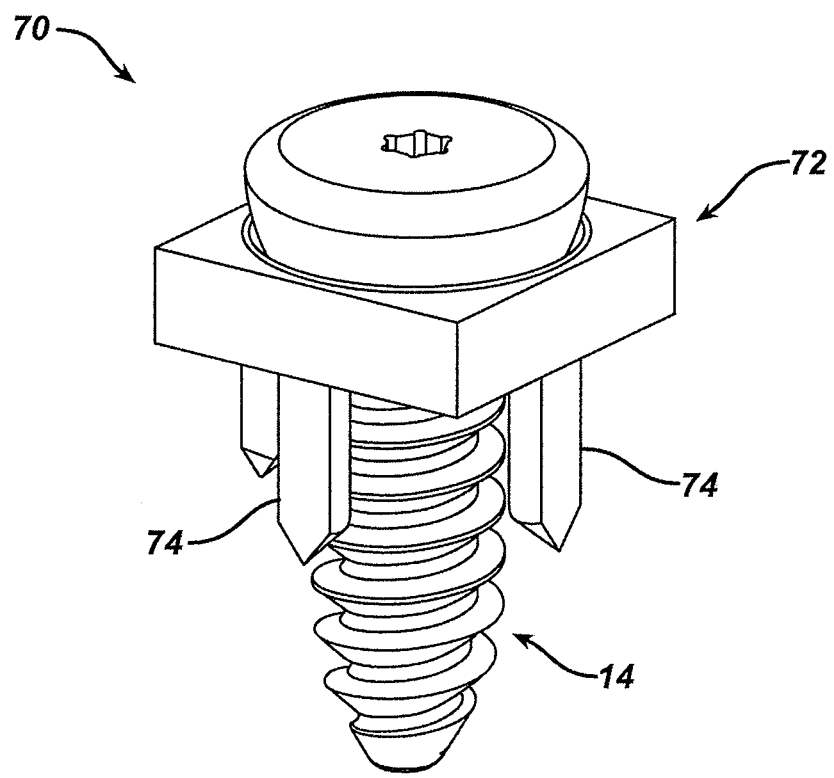
FIG. 6 is a perspective view of an alternative embodiment of a stabilization member of a spinal implant.

In other embodiments, the stabilization member of the implant 60 can be configured in various alternative shapes and sizes as compared to those substantially circular embodiments discussed above. For example, as shown in FIG. 6, the spinal implant 70 can include a stabilization member 72 configured in a substantially square shape. Like above, the stabilization member 72 can include a plurality of features 74 protruding therefrom capable of securing the implant to the desired anatomical location. Those skilled in the art will appreciate that in addition to substantially circular and square shapes, the stabilization member can be substantially oval, rectangular, or any other such shape and remain within the spirit and scope of the present invention.

Figure 7:
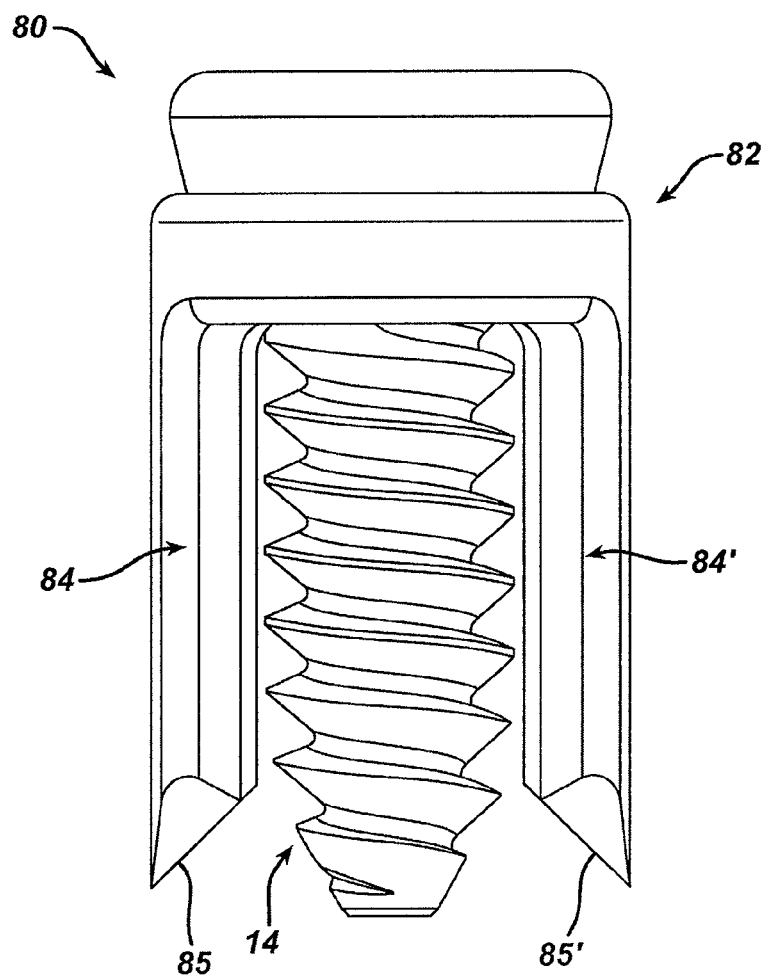
FIG. 7 is a front view of another alternative embodiment of a spinal implant.

In addition to engaging and/or piercing a portion of the facet joint, various embodiments of the spinal implant can include a stabilization member having a feature adapted to be positioned between the facet faces and adjacent the elongate member. For example, FIG. 7 provides a spinal implant 80 which includes a stabilization member 82 having opposing features 84, 84' adapted to extend along the length of the screw. As shown, the features 84, 84' can be positioned on opposite sides of the elongate member as the member is positioned within the facet joint. As such, the features 84, 84' can engage opposing facet faces thereby acting as a mechanical spacer. Further, the features 84, 84' can each terminate in a tapered distal region 85, 85' adapted to facilitate placement of the implant 80 within the facet joint. Those skilled in the art will appreciate that these features 84, 84' can include any size, length, and/or configuration capable of being positioned as described above. Alternatively, the stabilization member 82 can include only a single feature 84 adapted to be positioned between the facet faces and adjacent the elongate member.

Figure 8:
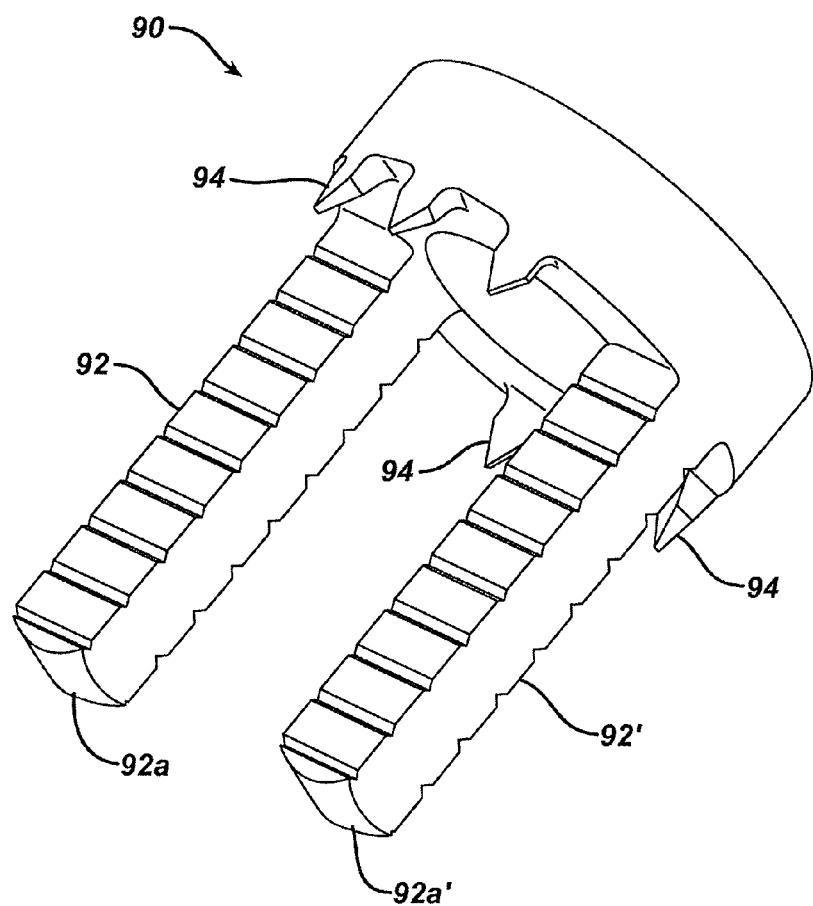
FIG. 8 is a perspective view of yet another embodiment of a spinal implant.

Referring to FIG. 8, the stabilization member 90 can include features 92, 92' adapted to be positioned between the facet faces and adjacent the elongate member, and also features 94 (e.g., tines) adapted to pierce an outer edge of the joint. Like the embodiments discussed above, such a stabilization member 90 can include any number of elongate features 92 in addition to any number and/or configuration of second feature 94. As further illustrated in FIG. 8, the elongate features 92, 92' can have a different configuration as compared to the elongate features 84, 84' of FIG. 7. More specifically, the features 92, 92' are substantially rectangular in shape and maintain a substantially constant thickness along their length. Also, features 92, 92' terminate at blunt distal ends 92a, 92a' thereby facilitating stabilization of the implant within a larger facet joint.

In addition to the various implants discussed above, the stabilization member can also be configured to include at least one lateral extension that can be in the form of a "plate-like" configuration, or it can be in the form of a tether or cable.

Figure 9A:
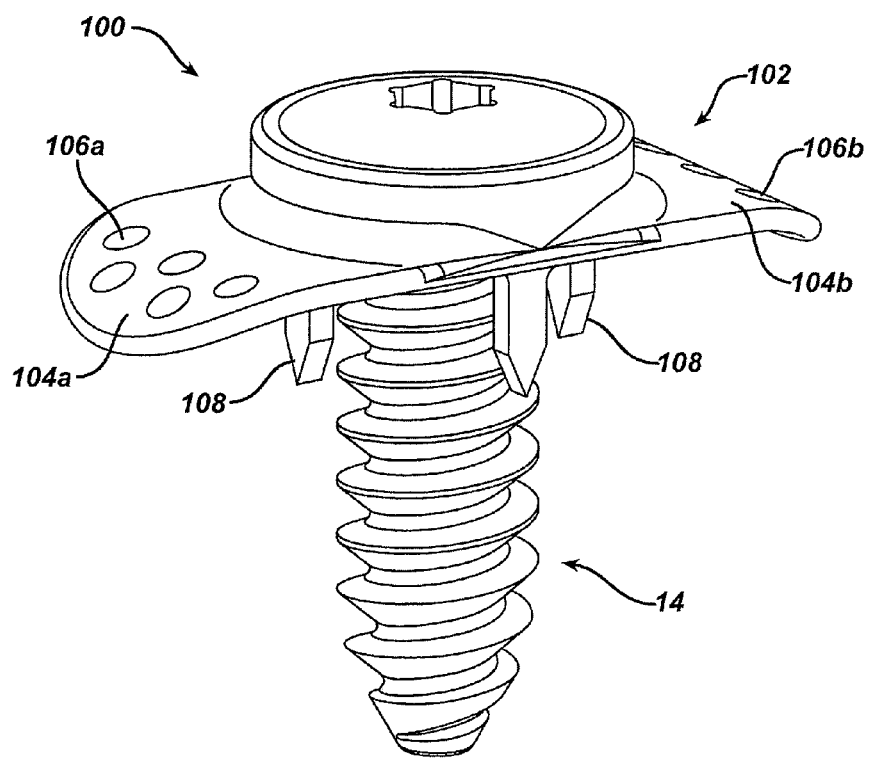
FIG. 9A is a perspective view of another embodiment of a spinal implant.
Figure 9B:
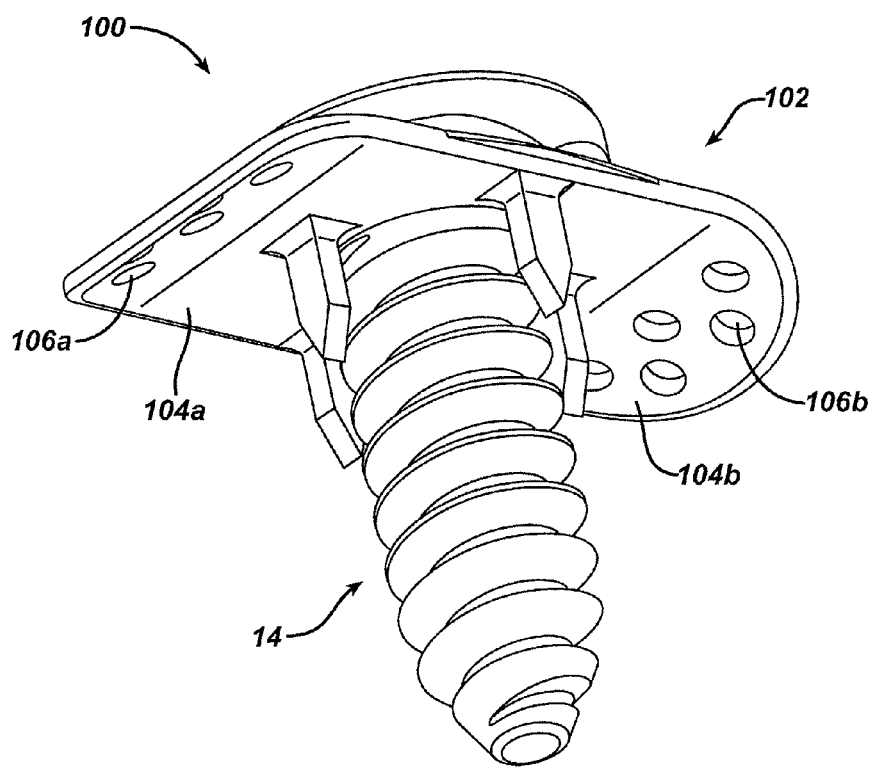
FIG. 9B is an alternative view of the spinal implant of FIG. 9A.

Such embodiments can be utilized in either intra-facet and/or trans-facet stabilization of the facet joint. As will be discussed, a plate like configuration allows for at least one lateral extension to be positioned adjacent to an outer portion of a vertebra and adapted to secure the implant to the vertebra (e.g., via a fixation member, sharpened prong, etc). For example, FIGS. 9A and 9B provide a spinal implant 100 wherein the stabilization member 102 includes a first lateral extension 104a and a second lateral extension 104b. As shown, the lateral extensions 104a, 104b can be positioned on opposite sides of the elongate screw 14. In other embodiments, the stabilization member 102 can include only a single lateral extension 104a. In still other embodiments, the lateral extensions can be stacked relative to one another. As will be appreciated by those skilled in the art, the lateral extensions can include various other configurations relative to one another and remain within the spirit and scope of the present invention.

The first lateral extension 104a includes at least one opening 106a adapted to receive a fixation member (e.g., a bone screw, a pin, etc.) thereby allowing the fixation member to pass through the lateral extension 104a and securely engage (e.g., screw into) an underlying vertebra. Similarly, the second lateral extension 104b can also include at least one opening 106b adapted to receive a second fixation member thereby allowing the second fixation member to pass through the second lateral extension 104b and securely engage a second vertebra. For example, as the elongate member 14 is positioned within the facet joint in an intra-facet configuration, the first lateral extension 104a can reside adjacent a superior vertebra (positioned above the facet joint) and the second lateral extension 106b can be positioned adjacent an inferior vertebra (positioned below the facet joint). In addition to these lateral extension features 104a, 104b, the stabilization member 102 can also include at least one tine 108 adapted to engage an outer edge of the facet joint.

Figure 10A:
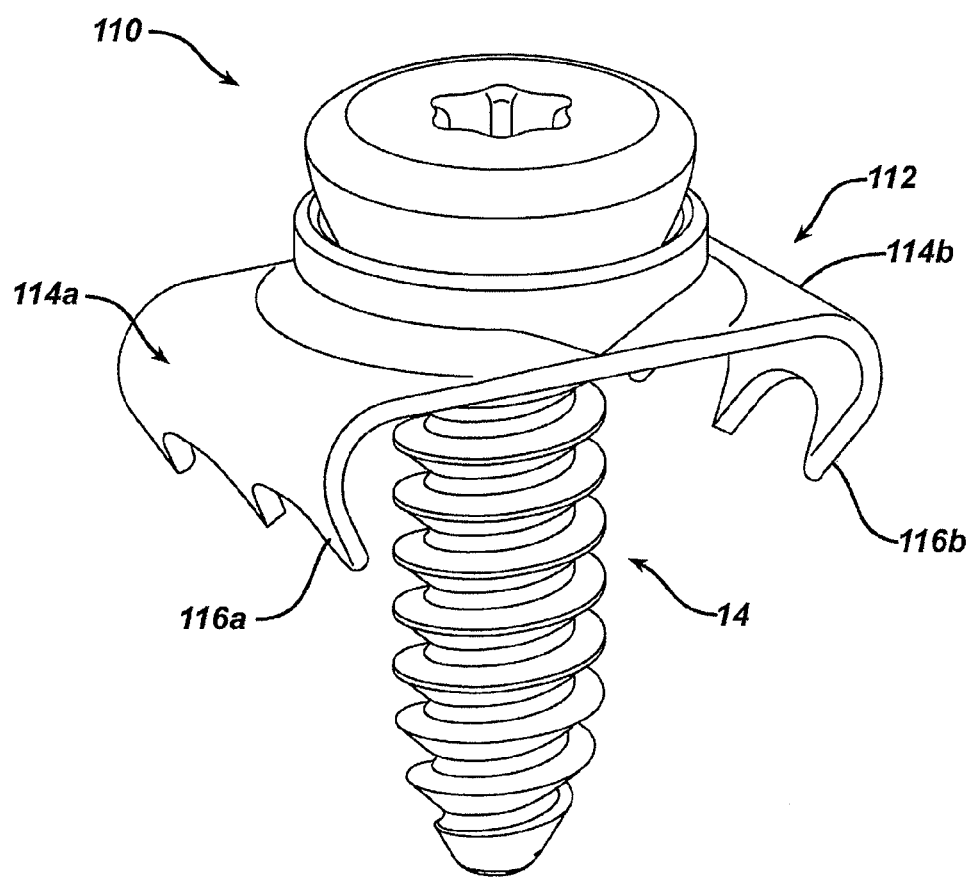
FIG. 10A is a perspective view of another embodiment of a spinal implant.
Figure 10B:
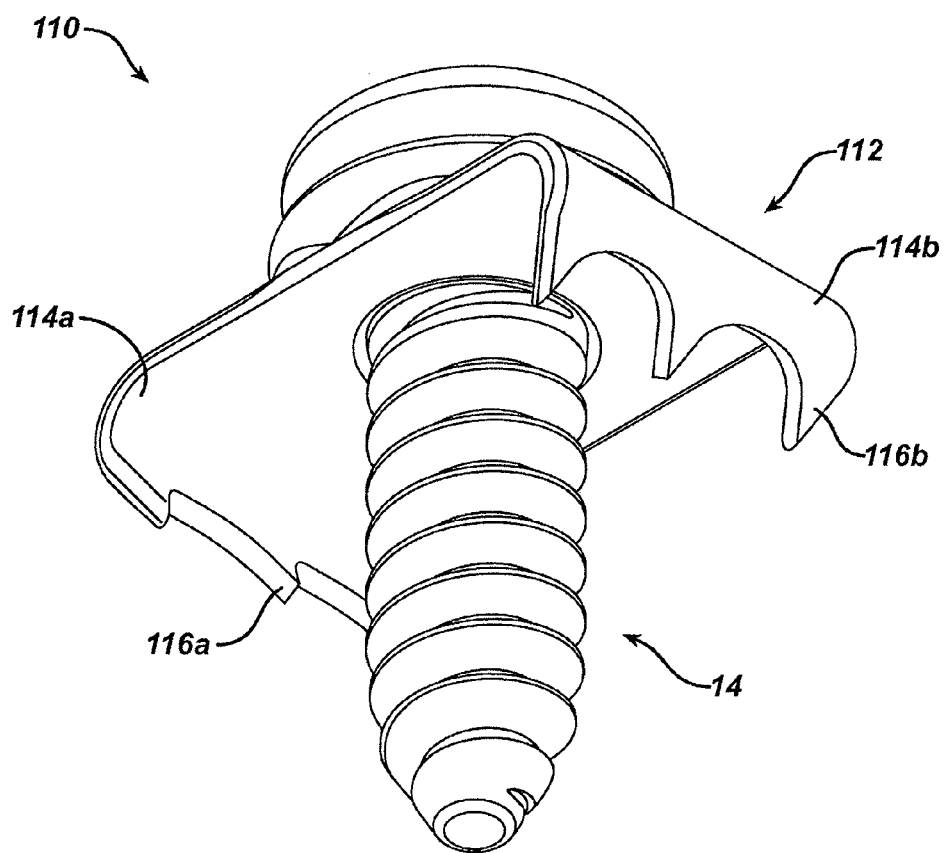
FIG. 10B is an alternative view of the spinal implant of FIG. 9B.

FIGS. 10A-10B provide another embodiment of the spinal implant 110 wherein the stabilization member 112 again includes a first lateral extension 114a and a second lateral extension 114b. Like above, these embodiment can be utilized for trans-facet delivery in addition to intra-facet delivery. However, in this embodiment, the first lateral extension 114a is adapted to include at least one (or a plurality of) pointed protrusion(s) 116a capable of engaging a vertebra as the screw 14 is positioned within the facet joint. Likewise, the second lateral extension 114b is also adapted to include at least one (or a plurality of) pointed protrusion(s) 116b capable of engaging a second adjacent vertebra as the elongate member is positioned within the facet joint in an intra-facet configuration. Those skilled in the art will appreciate that various other "plate-like" embodiments are within the spirit and scope of the present invention.

Such lateral extensions can adopt a variety of configurations. For example, the extensions can be planar, curvilinear, etc. Additionally, the extensions can be a "formable" material (e.g. an in situ curing polymer composite system) thereby allowing the extension to adopt a variety of shapes. One skilled in the art will appreciate that a variety of formable materials can be used. Examples of such formable materials can include in situ curable polymers (e.g., polymethylmethacrylate (PMMA) putty), superelastic alloys, shape memory materials, and braided cable.

The various stabilization members and feature(s) (e.g., tines, elongate features, plates, etc.) discussed above can include a wide-range of biocompatible materials. For example, the members and features can include various polymers or polymer blends, metals or metal alloys. With specific regards to the various features, these elements can include materials capable of piercing bone. Also, various features can be formed from a resilient material (e.g., a shape memory metal) thereby allowing the feature to conform to and/or "push back" against a facet face as the feature is wedged between the elongate member and the facet face (or outer edge of the facet joint). Also, as mentioned above, the stabilization member of the various embodiments can include a bioactive fusion-promoting material capable of actively participating in spinal fusion. For example, those features configured to be positioned within the facet joint (see FIGS. 7 and 8) can be formed from such a bioactive material thereby allowing the implant to participate in spinal fusion. Additionally, all other implants discussed above can include a portion (or a coating) having the bio-active fusion promoting material.

The fusion-promoting bioactive material can include any material capable of actively participating in spinal fusion. In an exemplary embodiment, the bioactive material can be allograft bone material (such as Allowashed™ available from LifeNet, Inc.; Virginia Beach, Va.). In another example, the material can be a bioresorbable plastic (poly-lactic acid, polyglycolic acid, their derivatives and/or blends), poly-anhydride (PolymerDrug™ by PolyMerix, Piscataway, N.J.), polymerized sugars or starches (Eureka™ by Surmodics of Eden Prairie, Minn.), bioceramic (HIP Vitox™ alumina or Zyranox™ zirconia by Morgan Advanced Ceramics of Fairfield, N.J.; crystalline hydroxyapatite, tricalcium phosphates or combinations of these materials by Berkeley Advanced Biomaterials of San Leandro, Calif.), bioceramic-loaded bioabsorbable material, or dense protein (Novasilk™ by Protein Polymer Technologies of San Diego, Calif.). Exemplary embodiments of such bioabsorbable materials include Biocryl™ (an 85% PLA/PGA, 15% tricalcium phosphate material available from Depuy Mitek, a Johnson & Johnson Company; Raynham, Mass.) or TriABSorb™ (a 5% hydroxyapatite, 95% PLA material available from Depuy Mitek, a Johnson & Johnson Company; Raynham, Mass.) As another example, the material can be an osseointegrating polymer such as PEEK/Optima™ (available from Invibio, Inc.; Greenville, S.C.). Those skilled in the art will appreciate that any combination of these materials are within the spirit and scope of the present invention. As will be discussed below, the screw can also include such fusion-promoting material thereby providing various embodiments capable of providing both spinal fixation and fusion.

The various spinal implants discussed above also include an elongate member coupled to the stabilization member. The elongate member can include any such member known to those skilled in the art. For example, the elongate member can include a pin, a dowel, a plug, a beam, a post, a threaded post, a bolt, an expansion barrel, a pop-rivet, a staple, an anchor, a suture (attached to a deep anchor or feature), etc. In an exemplary embodiment, the elongate member is a screw. As will be shown, the screw 14 can be configured (e.g., length, width, major diameter, minor diameter, etc) for placement within a facet joint in an intra-facet configuration. In other embodiments, the screw can be adapted for trans-facet spinal fixation and stabilization. As illustrated in FIGS. 1A-1C, the screw 14 includes a shank 15 extending between proximal 25 and distal ends 24. A portion of the distal end 24 can include a conical tip 23 capable of facilitating placement of the screw 14 within the facet joint. In one embodiment, the distal tip 26 can include a blunt surface. In other embodiments, the distal tip 26 includes a sharp point (not shown).

The proximal end 25 of the screw 14 can be adapted so as to prevent over-insertion of the screw thereby substantially preventing injury resulting from penetration of the screw into the spinal column. As will be apparent to one skilled in the art, the proximal end 25 can be adapted in various ways to prevent such over-insertion. For example, as shown in FIGS. 1A-1C, the proximal end 25 can include a screw head 22 extending from the proximal end of the shank, the head 22 having a diameter greater than a major diameter ($D_1$) of the shank. Additionally, as discussed in detail above, the stabilization member and associated stabilization feature substantially prevent over-insertion of the implant by engaging portions of the stabilization member to various bony portions associated with the facet joint (e.g., facet faces, outer portion of facet, outer edge of facet, etc.). The screw head 22 can be a distinct element or can be integral with the screw. As discussed above, in an exemplary embodiment, the screw head 22 can be adapted to allow for polyaxial coupling of the stabilization member 12. Those skilled in the art will appreciate that various screw head 22 designs are within the spirit and scope of the present invention.

As further shown in FIGS. 1A-1C, the shank 15 can have a thread 20 formed thereon with a configuration such that a major diameter ($D_1$) and a minor diameter ($D_2$) of the thread 20 can remain substantially uniform in the direction from the distal tip 23 to the proximal end 25 of the shank 15. In another embodiment (not shown), the major diameter of the screw 100 can increase from the distal 24 to proximal end 25 of the shank 15. The thread 20 can be continuous or non-continuous. In the exemplary embodiment of FIGS. 1A-1C, the thread 20 begins proximal to the distal tip 26 and proceeds along substantially the entire length of the shank 15, terminating before the head 22. In an alternative embodiment, the thread 20 can extend along the entire distal end 24. One skilled in the art will appreciate that the thread 20 can be configured to run clockwise or counter-clockwise.

The threads can include various sizes and/or dimensions. In an exemplary embodiment, the threads have a buttress cross-section, and a substantially constant thread crest height, thickness, and pitch along the length of the screw. In one embodiment, the root diameter of the screw can be proportional to the facet distraction distance after screw placement within the joint. Further, the thread depth relates to bony purchase and correlates to screw extraction strength. Such features can be optimized for stabilization of the facet joint via placement of the screw within the facet joint in an intra-facet configuration.

Various dimensions of the screw are within the spirit and scope of the present invention. In an exemplary embodiment, the dimensions of the screw (e.g., length, major diameter, minor diameter, etc.) are adapted for placement of the implant within a facet joint in an intra-facet or trans-facet configuration, whichever is required for a desired procedure. Referring to those embodiments utilizing intra-facet placement, the screw can have a length in the range of about 25 mm to about 30 mm, a major diameter ($D_1$) in the range of about 4 mm to about 12 mm, and a minor diameter ($D_2$) in the range of about 2 mm to about 8 mm. Additionally, the distance between adjacent thread heights can be in the range of about 1 mm to about 5 mm. Those skilled in the art will appreciate that various screw dimensions are within the spirit and scope of the present invention.

Referring to FIG. 1B, the proximal facing surface of the screw head 22 can include a drive feature 28 capable of receiving (or being received by) a driver instrument (e.g., a screwdriver) for delivery of the screw to the facet joint. The drive feature 28 can be of any suitable design as is known in the art. For example, the drive feature 28 can be a female drive feature, such as a hex-shaped socket, capable of seating a complementary male drive feature of a driver tool. Similarly, the drive feature 28 can be a male feature (not shown) capable of mating with a complementary female drive feature of a driver tool. Regardless of the shape or configuration of the drive feature 28, it should be effective to enable application of a torque along the entire shaft of the screw using a suitable driver tool.

As shown in FIG. 1C, the screw 10 can be a cannulated screw that includes an inner lumen 29 that extends along its entire length. The lumen can be of any suitable diameter, but in one embodiment it is capable of receiving a Kirschner wire ("K-wire"), which can serve as a guide-wire for delivery of the cannulated screw to the facet joint.

In addition to the embodiments described herein, the screw can include a wide range of geometries. For example, the screw can have an undulating geometry wherein either the minor diameter varies and the thread size remains substantially constant, or the minor diameter remains substantially constant and the major diameter varies from proximal to distal ends. Various such configurations are described in U.S. Provisional Patent Application No. 60/891,616, filed on Feb. 26, 2007, entitled "Facet Fixation and Fusion Screw and Method of Use," the entirety of which is incorporated herein by reference.

The elongate screw, like the stabilization member described above, can be adapted to allow for spinal fusion as well as spinal fixation. As such, any portion of the elongate screw can include or be formed of a fusion-promoting bioactive material so that the screw actively participates in spinal fusion. In an exemplary embodiment, the screw is made from the bioactive material. In another embodiment, a bioactive material can be formed as a coating on a non-bioactive material from which the screw is formed. For example, the screw can be formed of a metal or metal allow and be coated with a fusion-promoting bioactive material. In an alternative embodiment, the non-fusion promoting material (e.g., metal or metal alloy) can form a "cage-like" device capable of housing and releasing the fusion-promoting material. A benefit of these embodiments is the added stability provided by the non-fusion material.

Like above, the fusion-promoting bioactive material can include any material capable of actively participating in spinal fusion. In an exemplary embodiment, the bioactive material can be allograft bone material (such as Allowashed™ available from LifeNet, Inc.; Virginia Beach, Va.). In another example, the material can be a bioresorbable plastic (polylactic acid, polyglycolic acid, their derivatives and/or blends), poly-anhydride (PolymerDrug™ by PolyMerix, Piscataway, N.J.), polymerized sugars or starches (Eureka™ by Surmodics of Eden Prairie, Minn.), bioceramic (HIP Vitox™ alumina or Zyranox™ zirconia by Morgan Advanced Ceramics of Fairfield, N.J.; crystalline hydroxyapatite, tricalcium phosphates or combinations of these materials by Berkeley Advanced Biomaterials of San Leandro, Calif.), bioceramic-loaded bioabsorbable material, or dense protein (Novasilk™ by Protein Polymer Technologies of San Diego, Calif.). Exemplary embodiments of such bioabsorbable materials include Biocryl™ (an 85% PLA/PGA, 15% tricalcium phosphate material available from Depuy Mitek, a Johnson & Johnson Company; Raynham, Mass.) or TriABSorb™ (a 5% hydroxyapatite, 95% PLA material available from Depuy Mitek, a Johnson & Johnson Company; Raynham, Mass.) As another example, the material can be an osseointegrating polymer such as PEEK/Optima™ (available from Invibio, Inc.; Greenville, S.C.). Those skilled in the art will appreciate that any combination of these materials are within the spirit and scope of the present invention.

The non-fusion promoting material can be any suitable biocompatible material. For example, the non-fusion promoting material may be a metal or metal alloy. In an exemplary embodiment, the non-fusion promoting material is titanium or a titanium alloy (i.e., Ti 6A1 4V). Those skilled in the art will appreciate that various other such biocompatible materials are within the spirit and scope of the present invention.

Figure 11:
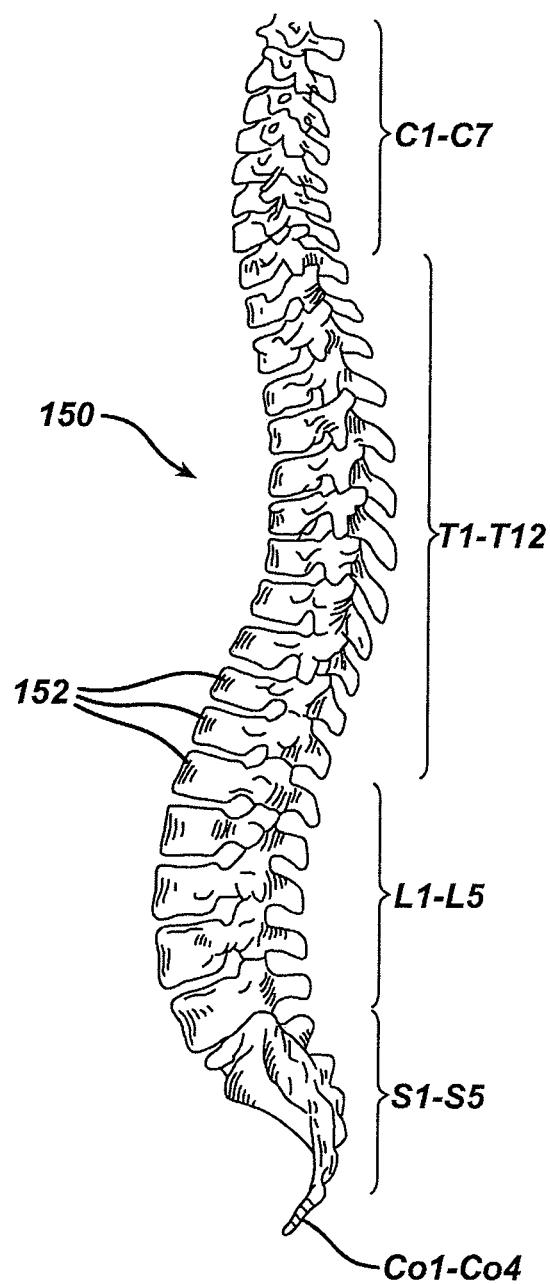
FIG. 11 is a representation of a human spinal column.
Figure 12:
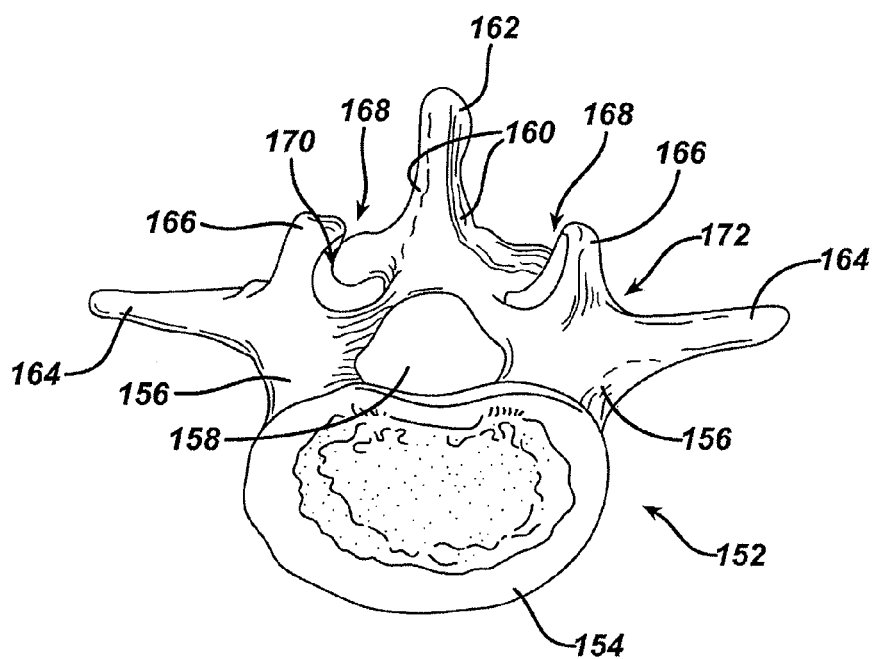
FIG. 12 is a representation of a lumbar vertebra.
Figure 13:
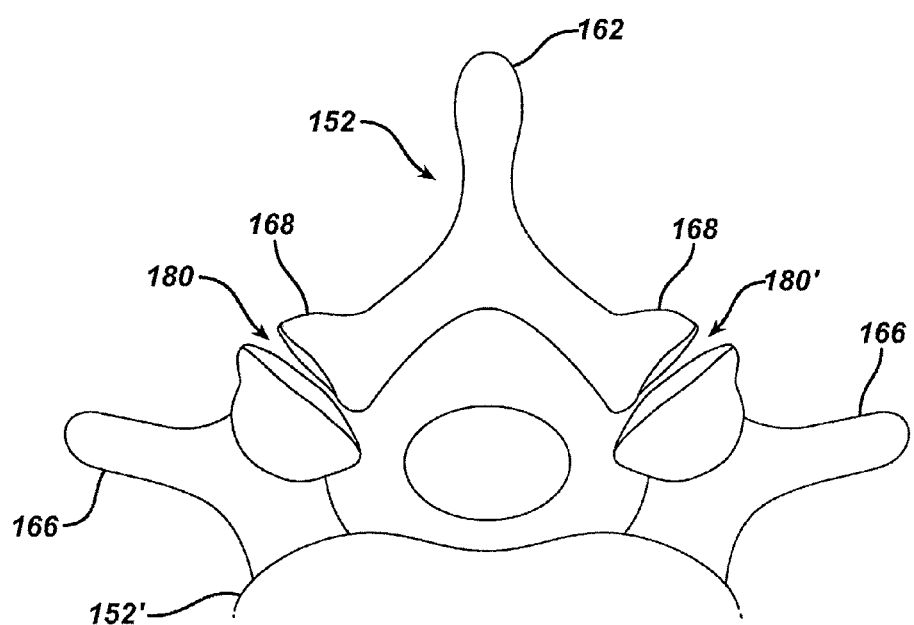
FIG. 13 is a representation of a first facet joint and a corresponding second facet joint formed as a result of a first vertebra stacked on a second vertebra.

In addition to the spinal implants discussed above, a method for providing stabilization and/or fusion to a facet joint is herein provided. Before describing the presently disclosed method, the following provides an overview of facet joint anatomy and prior art methods of providing spinal fixation to such joint. As such, FIGS. 11-13 are an overview of the spinal column structure and location of associated facet joints. As FIG. 11 shows, the human spinal column 150 is comprised of a series of thirty-three stacked vertebrae 152 divided into five regions. The cervical region includes seven vertebrae 152, known as C1-C7. The thoracic region includes twelve vertebrae 152, known as T1-T12. The lumbar region contains five vertebrae 152, known as L1-L5. The sacral region is comprised of five vertebrae 152, known as S1-S5. The coccygeal region contains four vertebrae 152, known as Co1-Co4.

FIG. 12 shows a normal human lumbar vertebra 152. Although the lumbar vertebrae 152 vary somewhat according to location, they share many features common to most vertebrae 152. Each vertebra 152 includes a vertebral body 154. Two short bones, the pedicles 156, extend posteriorly from each side of the vertebral body 154 to form a vertebral arch 158. At the posterior end of each pedicle 156 the vertebral arch 158 flares out into broad plates of bone known as the laminae 160. The laminae 160 fuse with each other to form a spinous process 162, to which muscle and ligaments attach. A smooth transition from the pedicles 156 into the laminae 160 is interrupted by the formation of a series of processes.

Two transverse processes 164 thrust out laterally on each side from the junction of the pedicle 156 with the lamina 160. The transverse processes 164 serve as levers for the attachment of muscles to the vertebrae 152. Four articular processes, two superior 166 and two inferior 168, also rise from the junctions of the pedicles 156 and the laminae 160. The superior articular processes 166 are sharp oval plates of bone rising upward on each side from the union of the pedicle 156 with the lamina 160. The inferior processes 168 are oval plates of bone that jut downward on each side. The superior and inferior articular processes 166 and 168 each have a natural bony structure known as a facet. The superior articular facet 70 faces upward, while the inferior articular facet 172 faces downward. As shown in FIG. 13, when adjacent vertebrae 152, 152' are aligned (i.e., stacked), the facets interlock to form corresponding facet joints 180, 80' positioned at the same level of the spine.

Figure 14A:
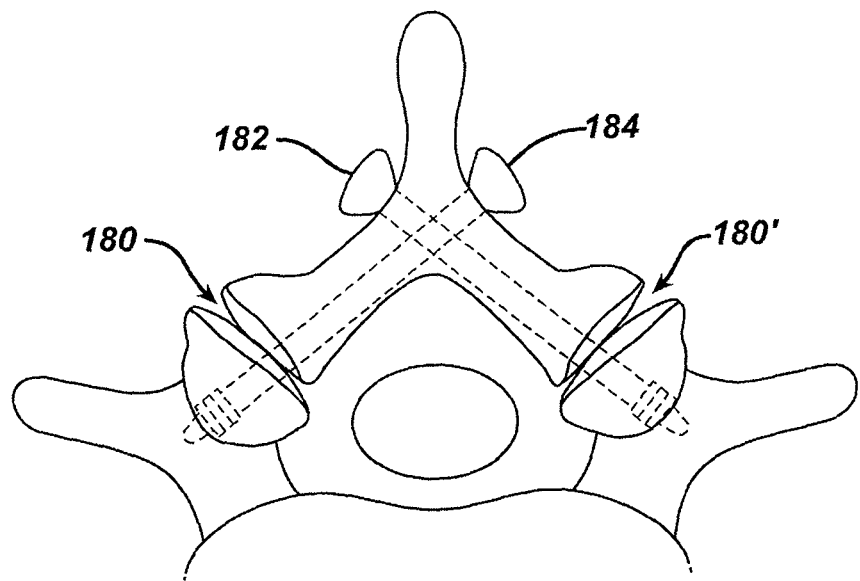
FIG. 14A is a representation of prior art trans-facet delivery of fixation screws.
Figure 14B:
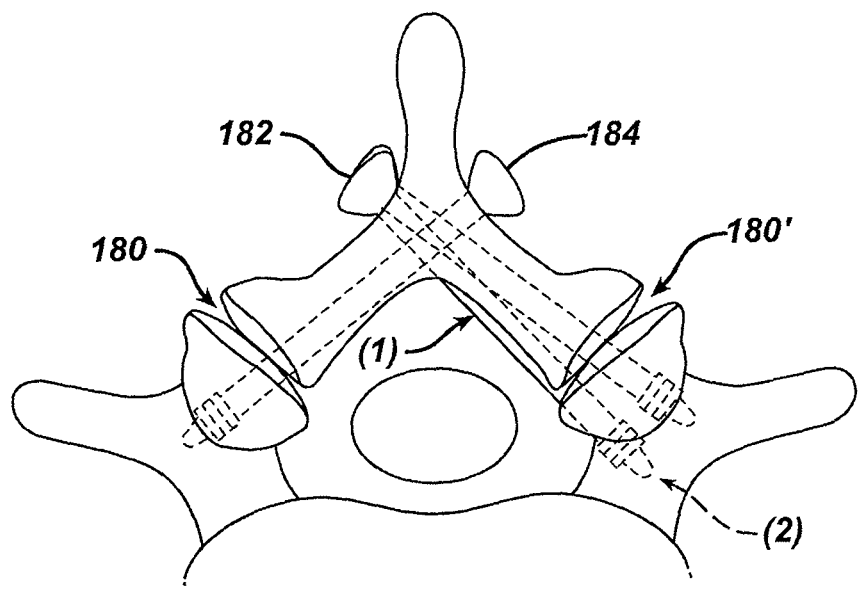
FIG. 14B is a representation of prior art trans-facet delivery of fixation screws wherein one of the trans-facet screws has impinged the spinal column.
Figure 14C:
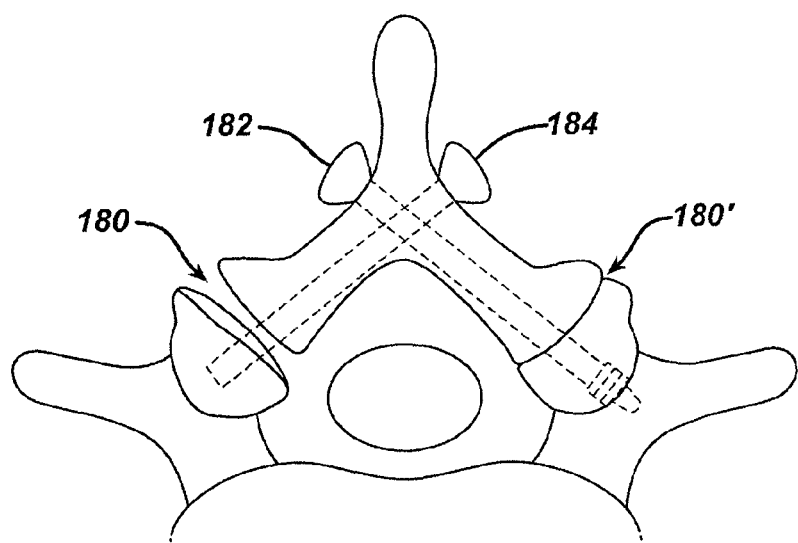
FIG. 14C is a representation of prior art trans-facet delivery of fixation screw wherein incorrect placement of the trans-lamina screws results in rotational distortion of the joint.

Looking in more detail at FIG. 13, the spinous process 162 and inferior articular processes 168 of the top vertebrae 152 are positioned adjacent to the superior articular processes 166 of the bottom vertebrae 152' and form facet joints 180, 180'. As shown in FIG. 14A, prior art trans-facet fixation procedure includes the insertion of trans-facet screws 182, 184 through bone and across the facet joints 180, 180'. However, such a procedure has been known to result in various problems. For example, FIG. 14B shows that a minor miscalculation in screw placement can result in a trans-facet screw 182 impinging upon the spinal column (as indicated by (1)) and/or impinging upon surrounding nerves (as indicated by (2)), thereby resulting in patient injury. Additionally, trans-facet screw placement procedures can result in unwanted and/or unpredictable rotational distortion (or lateral offset) of the facet joint because of the difficulty of approximating the final position of the trans-facet screws 182, 184 in these procedures. As shown in FIG. 14C, trans-facet placement of the screws 182, 184 can result in significantly different gap sizes in corresponding facet joints 180, 180', thereby resulting in unwanted tension on the spine and ultimately injury to the patient. As discussed, various embodiments of the spinal implant provided herein (e.g., the plate-like embodiments shown in FIGS. 9A-10B) can be utilized to improve such prior art trans-facet procedures.

Figure 15:
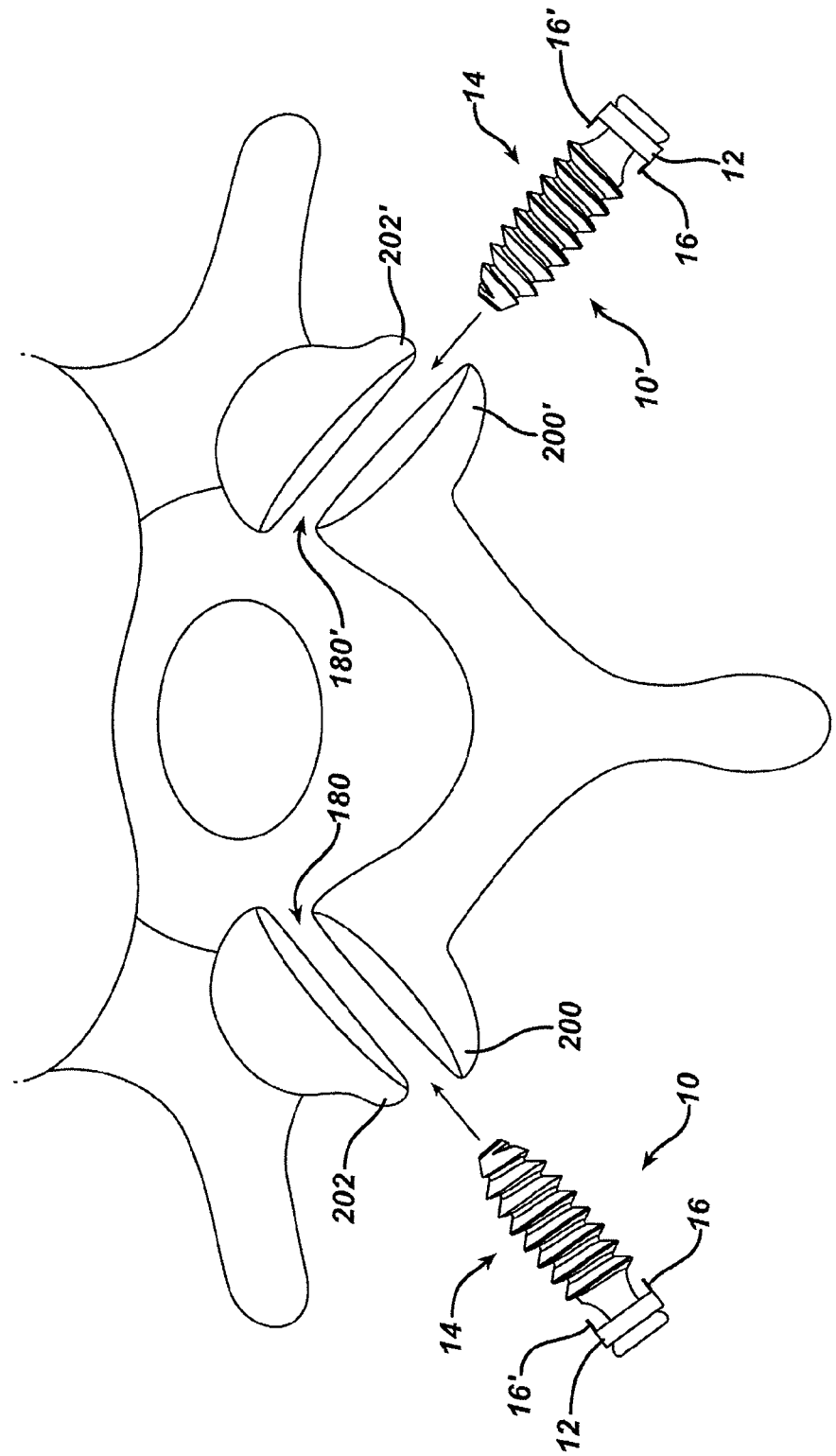
FIG. 15 is a representation of an implant being delivered to a facet joint in an intra-facet configuration.

FIG. 15 provides a representation of a first implant 10 being delivered to a first facet joint 180 in an intra-facet configuration, and a second implant 10' being delivered to a second, corresponding facet joint 180' (positioned at the same level of the spine as the first facet joint 180) in a similar intra-facet configuration. In this representation, the first 10 and second 10' implant are substantially identical. In other embodiments, the implants can be of different sizes (e.g., the first implant 10 larger than the second implant 10'), have different stabilization members, and/or different number, types or configurations of features incorporated into stabilization member. More specifically, any implant discussed above can be delivered to either corresponding facet joint 180, 180' and remain within the spirit and scope of the present invention. Furthermore, the method can include the delivery of only a single implant to only one of the corresponding facet joints 180, 180'.

Figure 16B:
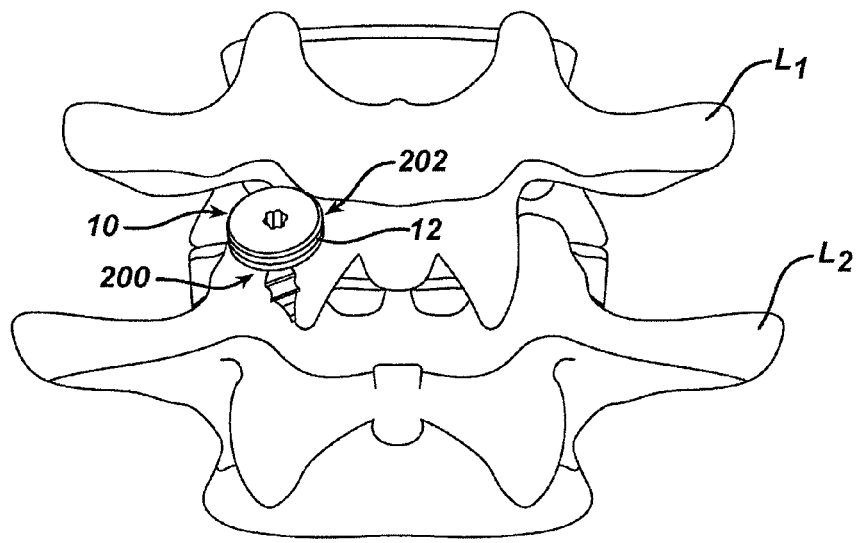
FIG. 16B is an alternative view of the embodiment of FIG. 16A.

FIG. 16A provides a representation showing the implants 10, 10' of FIG. 15 positioned within the facet joint in an intra-facet configuration. In other embodiments, the method includes delivering the implants to the facet joint in a trans-facet orientation. Referring to the intra-facet embodiments, as the implant 10 is positioned within the facet joint, the first tine 16 can be adapted to pierce a bony portion 200 of a first vertebra while a second tine 16' can be configured to pierce a bony portion 202 of a second vertebra thereby essentially acting as a staple to provide added stability to the facet joint. Also, as discussed above, the thread of the elongate member 14 can be configured to provide a desired amount of distraction to the joint. As shown, the second implant 10' can be similarly configured such that the first tine 16 of the second implant 10' pierces a bony portion of the first vertebra 200' and a second tine 16' of the second implant 10' pierces a bony portion 202' of the second vertebra. In addition to the embodiment represented in FIG. 16A, the features (tines) can be configured to wedge between the elongate screw 14 and an outer edge(s) 200a, 202a of the facet joint. An example of such a tine was described in FIG. 2 (see element 34 and associated discussion). FIG. 16B shows another view of the implant 10 being positioned within the facet joint (between adjacent vertebra, L1 and L2) wherein the stabilization member 12 engages a bony portion 202 of vertebra L1 and a bony portion 200 of vertebra L2 so as to secure the implant 10 within the facet joint in an intra-facet configuration. In each embodiment, the tines can be adapted to contact (engage and/or pierce) various anatomical structures such as bone, tissue, etc. Engaging any such structure is within the spirit and scope of the present invention.

Figure 16C:
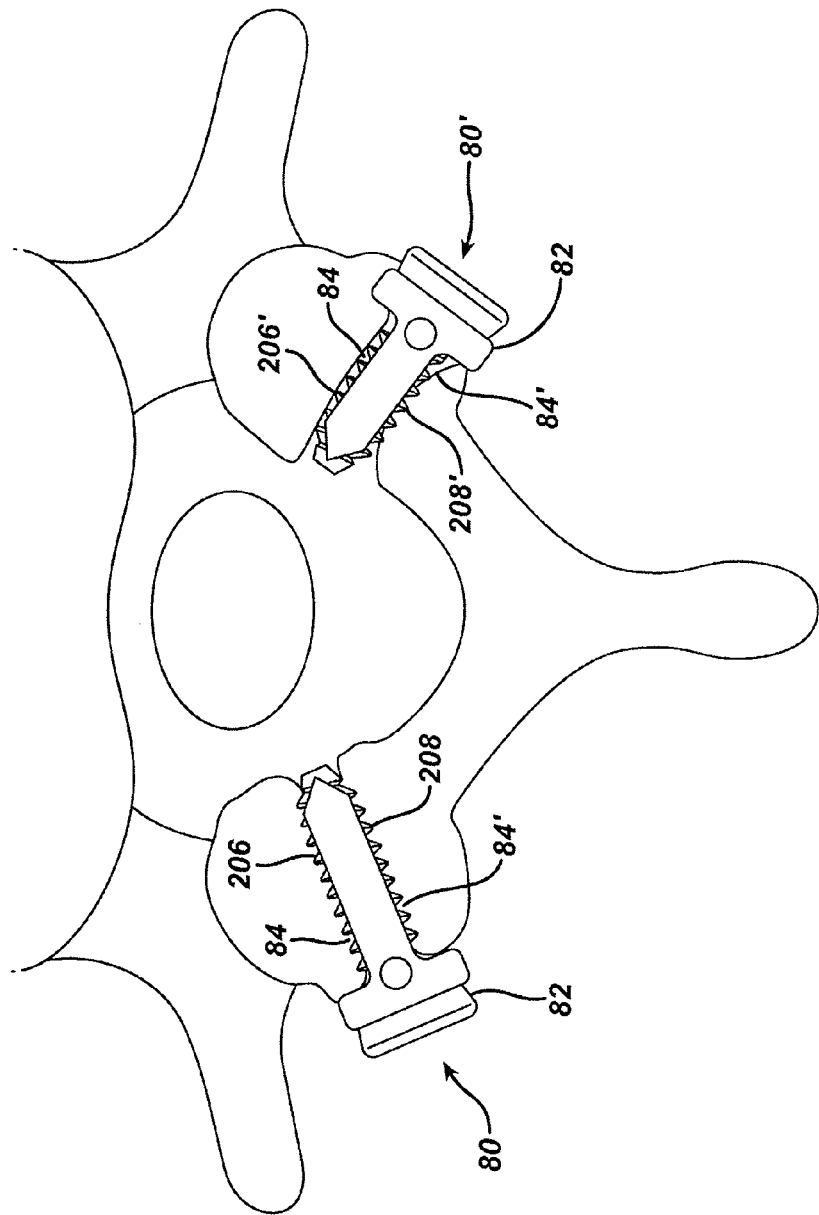
FIG. 16C is a representation of the implant of FIG. 7 being positioned within the facet joint in an intra-facet configuration.

FIG. 16C provides another embodiment of an implant(s) 80, 80' being positioned within the facet joint in an intra-facet configuration. More specifically, the implant 80 (shown and described in relation to FIG. 7) includes a stabilization member 82 having a first feature 84 and a second feature (hidden from view) configured to extend along a substantial length of the screw 14 such that the first elongate feature 84 and the second elongate member 84' are positioned between the facet joints and adjacent to opposite sides of the elongate member.

In these embodiments, the features 84, 84' can act as mechanical keys thereby contributing to stabilization of the joint. In addition, forming these features 84, 84' of a fusion/promoting material can allow for spinal fusion as well as fixation. In other embodiments, the elongate features can be wedged between the elongate screw and a corresponding facet face.

As an added benefit, the intra-facet spinal implant and procedures disclosed herein are particularly well suited for minimally invasive surgery. That is, crews or similar devices can be positioned using one or more small, percutaneous incisions, with or without the need for an access port. Such procedures, which are generally well known to those skilled in the art, tend to result in less operative trauma for the patient than a more invasive procedures. Minimally invasive procedures also tend to be less expensive, reduce hospitalization time, causes less pain and scarring, speed recovery, and reduce the incidence of post-surgical complications, such as adhesions.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for facet joint fixation and fusion, comprising:
    surgically delivering an assembled spinal implant to a facet joint, the spinal implant including an integral, bone-engaging elongate member, the elongate member having threads extending over at least a portion thereof, the elongate member further seated within a stabilization member, the stabilization member having a bone contacting surface being configured to seat the elongate member, the stabilization member further having at least one feature configured to stabilize a portion of the facet joint and the spinal implant; and
    engaging the feature to an anatomical structure thereby securing the spinal implant relative to the facet joint and engaging the threads of the spinal implant such that the threads abut against a superior articular facet and an inferior articular facet.

2. The method of claim 1, further comprising delivering a first spinal implant to a first facet joint and a second spinal implant to a second, corresponding facet joint at the same level of a spine.

3. The method of claim 1, wherein the surgically delivering step is conducted in a minimally invasive surgical procedure.

4. The method of claim 1, wherein the spinal implant includes a fusion-promoting bioactive material.

5. The method of claim 1, wherein surgically delivering an assembled spinal implant includes surgically delivering an assembled implant capable of polyaxial movement.

6. The method of claim 1, wherein the stabilization member has a lateral extension, the at least one feature extending distally therefrom, and wherein the method further comprises delivering a fixation member through an opening extending through the lateral extension.

* * * * *